United States Patent [19]
Weis et al.

[11] Patent Number: 5,677,439
[45] Date of Patent: *Oct. 14, 1997

[54] OLIGONUCLEOTIDE ANALOGUES CONTAINING PHOSPHATE DIESTER LINKAGE SUBSTITUTES, COMPOSITIONS THEREOF, AND PRECURSOR DINUCLEOTIDE ANALOGUES

[75] Inventors: Alexander Ludvik Weis, Berwyn, Pa.; Frederick Herman Hausheer, San Antonio, Tex.; Prasad Venkata Chala Chaturvedula, Exton, Pa.; Daniel Joseph Delecki, Radnor, Pa.; Paul Francis Cavanaugh, Jr., West Chester, Pa.; Patricia Susan Moskwa, Phoenixville, Pa.; Fred Terry Oakes, Rochester, N.Y.

[73] Assignee: Sanofi, Paris, France

[*] Notice: The term of this patent shall not extend beyond the expiration date of Pat. No. 5,245,022.

[21] Appl. No.: 449,124

[22] Filed: May 24, 1995

Related U.S. Application Data

[62] Division of Ser. No. 205,335, Mar. 3, 1994, abandoned, which is a continuation of Ser. No. 682,784, Apr. 9, 1991, abandoned, which is a continuation-in-part of Ser. No. 562,180, Aug. 3, 1990, Pat. No. 5,245,022, Ser. No. 582,287, Sep. 13, 1990, abandoned, Ser. No. 582,456, Sep. 13, 1990, abandoned, and Ser. No. 582,457, Sep. 13, 1990, abandoned.

[51] Int. Cl.$^6$ .................................. C07H 21/04
[52] U.S. Cl. .................. 536/23.1; 536/24.5; 514/44; 435/6
[58] Field of Search ................. 514/44; 536/24.5, 536/73.1

[56] References Cited

U.S. PATENT DOCUMENTS

| | | | |
|---|---|---|---|
| 5,138,045 | 8/1992 | Cook et al. | 536/24.5 |
| 5,214,134 | 5/1993 | Weis et al. | 536/25.3 |
| 5,223,618 | 6/1993 | Cook et al. | 544/276 |
| 5,245,022 | 9/1993 | Weis et al. | 536/24.5 |
| 5,378,825 | 1/1995 | Cook et al. | 536/25.34 |
| 5,389,023 | 2/1995 | Sanghvi et al. | 536/25.3 |
| 5,489,677 | 2/1996 | Sanghvi et al. | 536/22.1 |

OTHER PUBLICATIONS

Gura, "antisense Has Growing Pains—Efforts to Develop Antisense Compounds for Cancer, AIDS, and Other Diseases Have Encountered Some Unexpectd Questions About How the Drugs Really Work," *Science* 270, 575–577 (1995).
Krieg et al., "CpG Motifs in Bacterial DNA Trigger Direct B–Cell Activation," *Nature*, 374, 546–549 (Apr. 6, 1995).
Uhlmann et al., "Antisense Oligonucleotides: A New Therapeutic Principle," *Chem. Reviews*, 90(4), 543–584 (1990).
Cohen et al., "Antisense Oligonucleotides as Therapeutic Agents—Is the Bullet Really Magical?" *Science*, 261, 1004–1012 (1993).
Jager et al., "Oligonucleotide N-Alkylphosphoramidates: Synthesis and Binding to Polynucleotides," *Biochemistry*, 27(19), 7237–7246 (1988).

Agrawal et al., "Oligodeoxynucleoside methylphosphonates: Synthesis and Enzymatic Degradation," *Tetrahedron Letters*, 28(31), 3539–3542 (1987).
Goodchild et al., "Inhibition of Replication and Expresion of HIV–1 Tissue Culture by Oligodeoxynucleotide Hybridization Competition," in *Human Retroviruses, Cancer, and AIDS: Approaches to Prevention and Therapy*, Alan R. Liss, Inc., New York, NY, 1988, pp. 423–438.
Sarin et al., "Inhibition of Acquired Immunodeficiency Syndrome Virus by Oligodeoxynucleoside methylphosphonate," *Proc. Nat. Acad. Sci. USA*, 85, 7448–7451 (Oct. 1988).
Kibler–Herzog et al., "Duplex Stabilities of Phosphorothioate, Methylphosphonate, and RNA Analogs of Two DNA 14–Mers," *Nucleic Acids Research*, 19(11), 2979–2986 (1991).
Vaseur et al., "Oligonucleosides: Synthesis of a Novel Methylhydroxylamine–Linked Nucleoside Dimer and Its Incorporation into Antisense Sequences," *J. Am. Chem. Soc.*, 114, 4006–4007 (1992).
Mungall et al., "Carbamate Analogs of Oligonucleotides," *J. Organic Chem.*, 42(4), 703–706 (1977).
Stirchak et al., "Uncharged Stereoregular Nucleic Acid Analogues. I. Synthesis of a Cytosine–Containing Oligomer with Carbamate Internucleotide Linkages," *J. Organic Chem.*, 52(19), 4202–4206 (1987).
Maggio et al., "Synthese Regiospecifique D'Un Dinucleoside Ponte: (O$^6$–Desoxyguanosinyl)–1 (N$^4$–Desoxycytidyl)–2 Ethane," *Tetrahedron Letters*, 25(30), 3195–3198 (1984).
Gallo et al., "Alkyl Phosphotriester Modified Oligodeoxyribonucleotides. V. Synthesis and Absolute Configuration of Rp and S$_p$ Diastereoisomers of an Ethyl Phosphotriester (Et) Modified Eco RI Recognition Sequence, D[GGAA-(Et)TTCC]. A Synthetic Approach to Regio– and Stereospecific Ethylation–Interference Studies," *N Nucleic Acids Research*, 14(18), 7405–7420 (1986).
Coull et al., "Synthesis and Characterization of a Carbamate–Linked Oligonucleoside," *Tetrahedron Letters*, 28(7), 745–748 (1987).
Schneider et al., "Building Blocks for Oligonucleotide Analgos with Dimethylene Sulfide, Sulfoxide, and Sulfone Groups Replacing Phosphodiester Linkages," *Tetrahedron Letters*, 31(3), 335–338 (1990).
Ogilvie et al., "Synthesis of a Thymidine Dinucleotide Analogue Containing and Internucleotide Silyl Linkage," *Tetrahedron Letters*, 26(35), 4159–4162 (1985).
Cormier et al., "Synthesis of Hexanucleotide Analogues Containiing Diisopropylsilyl Internucleotide Linkages," *Nucleic Acids Research*, 16(1)), 4583–4594 (1988).

*Primary Examiner*—John Kight
*Assistant Examiner*—L. Eric Crane
*Attorney, Agent, or Firm*—Paul E. Dupont; William J. Davis; Imre Balogh

[57] ABSTRACT

The present invention relates to compounds, compositions and methods for inhibiting gene expression. The compounds of this invention comprise 1) oligonucleoside sequences of from about 6 to about 200 bases having a three atom internucleoside linkage or 2) oligonucleotide sequences of from about 9 to about 200 bases having a diol at either or both termini.

58 Claims, 7 Drawing Sheets

1a

1b

OLIGONUCLEOTIDE ANALOGUES CONTAINING PHOSPHATE DIESTER LINKAGE SUBSTITUTES, COMPOSITIONS THEREOF, AND PRECURSOR DINUCLEOTIDE ANALOGUES

CROSS REFERENCE TO RELATED APPLICATIONS

This application is a division of application Ser. No. 08/205,335, filed on Mar. 3, 1994, now abandoned which in turn is a continuation of application Ser. No. 07/682,784, filed Apr. 9, 1991, now abandoned, which in turn is a continuation-in-part of application U.S. Ser. No. 07/562,180, filed Aug. 3, 1990, now U.S. Pat. No. 5,245,822; application U.S. Ser. No. 07/582,287, filed Sep. 13, 1990, now abandoned; application U.S. Ser. No. 07/582,456, filed Sep. 13, 1990, now abandoned; and application U.S. Ser. No. 07/582,457, filed Sep. 13, 1990, now abandoned.

TECHNICAL FIELD

The present invention relates to compounds, compositions and methods for inhibiting gene expression. The compounds of this invention comprise 1) oligonucleoside sequences of from about 6 to about 200 bases having a three atom internucleoside linkage or 2) oligonucleotide sequences of from about 9 to about 200 bases having a diol at either or both termini.

BACKGROUND OF THE INVENTION

An antisense compound is a compound that binds to or hybridizes with a nucleotide sequence in a nucleic acid, RNA or DNA, to inhibit the function or synthesis of said nucleic acid. Because of their ability to hybridize with both RNA and DNA, antisense compounds can interfere with gene expression at the level of transcription, RNA processing or translation.

Antisense molecules can be designed and synthesized to prevent the transcription of specific genes to mRNA by hybridizing with genomic DNA and directly or indirectly inhibiting the action of RNA polymerase. An advantage of targeting DNA is that only small amounts of antisense compounds are needed to achieve a therapeutic effect. Alternatively, antisense compounds can be designed and synthesized to hybridize with RNA to inhibit post-transcriptional modification (RNA processing) or protein synthesis (translation) mechanisms. Exemplary target RNAs are messenger RNA (mRNA), transfer RNA (tRNA), ribosomal RNA (rRNA) and the like. Examples of processing and translation mechanisms include splicing of pre-mRNA to remove introns, capping of the 5' terminus of mRNA, hybridization arrest and nuclease mediated mRNA hydrolysis.

At the present time, however, the development of practical scientific and therapeutic applications of antisense technologies is hampered by a number of technical problems. Klausher, A., *Biotechnology*, 8:303–304 (1990). Synthetic antisense molecules are susceptible to rapid degradation by nucleases that exist in target cells. The oligonucleoside sequences of antisense DNA or RNA, for example, are destroyed by exonucleases acting at either the 5' or 3' terminus of the nucleic acid. In addition, endonucleases can cleave the DNA or RNA at internal phosphodiester linkages between individual nucleosides. As a result of such cleavage, the effective half-life of administered antisense compounds is very short, necessitating the use of large, frequently administered, dosages.

Another problem is the extremely high cost of producing antisense DNA or RNA using available semiautomatic DNA synthesizers. It has recently been estimated that the cost of producing one gram of antisense DNA is about $100,000. Armstrong, L., *Business Week*, Mar. 5, 1990, page 89.

A further problem relates to the delivery of antisense agents to desired targets within the body and cell. Antisense agents targeted to genomic DNA must gain access to the nucleus (i.e. the agents must permeate the plasma and nuclear membrane). The need for increased membrane permeability (increased hydrophobicity) must be balanced, however, against the need for aqueous solubility (increased hydrophilicity) in body fluid compartments such as the plasma and cell cytosol.

A still further problem relates to the stability of antisense agents whether free within the body or hybridized to target nucleic acids. Oligonucleotide sequences such as antisense DNA are susceptible to steric reconfiguration around chiral phosphorous centers.

Gene targeting via antisense agents is the inevitable next step in human therapeutics. Armstrong, supra at 88. The successful application of antisense technology to the treatment of disease however, requires finding solutions to the problems set forth above.

One approach to preparing antisense compounds that are stable, nuclease resistant, inexpensive to produce and which can be delivered to and hybridize with nucleic acid targets throughout the body is to synthesize oligonucleoside sequences with modifications in the normal phosphate-sugar backbone structure.

In general, two types of oligonucleoside sequences, with modified backbones have been reported. The first type includes modifications to the normal internucleoside phosphodiester linkage. The second type includes replacement of the phosphodiester linkage with non-phosphate internucleoside linkages. Uhlmann, E. and Peyman, A., *Chemical Reviews*, 9(4):544–584 (1990).

Modified phosphodiester linkages that have been reported to date are phosphorothioates, alkylphosphotriesters, methylphosphonates and alkylphosphoramidates.

Phosphorothioate modified phosphodiester linkages refer to phosphodiester bonds in which one or more of the bridging oxygen atoms is replaced by sulfur. Such linkages, however, are not suitable for use in antisense compounds. The retention of the chiral phosphorus center results in steric variation of monothioates. Further, both mono- and dithioates lack sequence specific hybridization and both are rapidly cleared from the plasma. The high affinity of phosphorothioates for glass and plastic also makes synthesis of these compounds difficult and inefficient.

Methyl- and ethylphosphotriesters have been prepared by reacting phosphodiester linked oligonucleosides with anhydrous methanol or ethanol. Miller, P. S. et al., *J. Am. Chem, Soc.*, 93:6657–6665(1971).

The triester linkage in oligodeoxyribonucleotide ethylphosphotriesters is stable under normal physiological pH conditions, although it can be hydrolyzed by strong acid or base. Methylphosphotriesters are less stable than ethyl- and other alkylphosphotriesters at neutral pH, owing to the possibility of nucleophilic displacement of the triester methyl group by solvent. Oligodeoxyribonucleotide ethylphosphotriesters appear to be completely resistant to hydrolysis by exonucleases and are not hydrolyzed by nucleases or esterases found in fetal bovine serum or human blood serum. Uhlmann, supra.

The methylphosphonates have several significant shortcomings in terms of therapeutic potential which include poor water solubility, chiral phosphorous centers, inability to control high yield stereoselective synthesis, rapid plasma clearance and urinary excretion.

Oligodeoxyribonucleoside phosphoramidates have internucleoside bonds containing nitrogen-phosphorus bonds. These nucleic acid analogs can be prepared from phosphoramadite intermediates or by oxidation of H-phosphonate intermediates in the presence of a primary or secondary amine. Preparation of the H-phosphonate analogs and the oxidation reaction can be readily carried out in a commercial DNA synthesizer.

A variety of non-ionic oligonucleoside sequences containing non-phosphate internucleoside linkages such as carbonate, acetate, carbamate and dialkyl- or diarylsilyl- derivatives have been synthesized and reported.

Although the carbonate linkage is resistant to hydrolysis by acid, it is rather easily cleaved with base, and thus special precautions are required for removal of the protecting groups at the end of the synthesis. While stable duplexes have been observed between poly(dA) analogs containing carboxymethyl internucleotide linkages and poly(U) analogs, other bases have not been studied. Thus, it is not known whether the fidelity of duplex formation with other bases will be perturbed by the carbonate linkage.

Internucleoside carbamates are reported to be more water soluble than other internucleoside bridges. The utility of carbamate linkages is limited, however, since thymine carbamates do not form hybrids with complementary DNA, while cytosine carbamates do not hybridize to guanine oligomers.

The carbamate linkage, like the carbonate linkage, is stable under physiological conditions. Unlike the carbonates, however, the carbamate linkage is stable to hydrolysis by bases, a property which simplifies the synthesis of oligomers containing this linkage. The carbamate linkage is resistant to nuclease hydrolysis.

Like the carbonate and acetate linkages, the carbamate linkage does not resemble the shape of the phosphodiester internucleotide bond. However, molecular models suggest that the linkage should allow the oligomer to assume conformations which would allow it to form hydrogen-bonded complexes with complementary nucleic acids. There are conflicting reports on the stability of duplexes formed by carbamate oligomers and complementary nucleic acids. A carbamate-linked oligomer containing six thymidine units does not form complexes with either A(pA)$_5$ or dA(pA)$_5$. On the other hand, a carbamate-linked oligomer containing six deoxycytosine units forms stable complexes with d-(pG)$_6$ and poly(dG).

The internucleoside linkage of dialkyl- or diphenylsilyl oligomer analogs closely resembles the tetrahedral geometry of the normal phosphodiester internucleotide bond. The oligomers are prepared in solution by reacting a suitably protected nucleoside-3'-O-dialkyl- or diphenylsilyl chloride or trifluoromethanesulphonyl derivative with a 3'-protected nucleoside in anhydrous pyridine. The former can be prepared by reaction of 5'-O-trityl nucleoside with dialkyl- or diphenyldichlorosilane or with the bis (trifluoromethanesulphonyl)diisopropylsilane.

Because the dialkyl- and diphenylsilyl linkages are sensitive to hydrolysis by acid, care must be taken in choosing protecting groups for the synthesis. Nucleoside dimers and hexamers having siloxane internucleoside linkages and a method of synthesizing such polymers have been reported by Ogilvie and Cormier. See, e,g., Ogilvie, K. K. and Cormier, J. F., *Tetrahedron Letters*, 26(35):4159–4162 (1985); Cormier J. F. and Ogilvie, K. K., *Nucleic Acids Research*, 16(10):4583–4594 (1988).

Although the carbonate, carbamate and silyl linked oligonucleoside sequences have the requisite nuclease resistance to make them attractive candidates as antisense reagents, their ability to function in this capacity has not yet been reported. Further, the ability of these oligomers to be taken up by cells in culture has not been reported. A potential drawback with these oligomers is their reported low solubility in aqueous solution. It is not clear whether sufficient concentrations can be obtained for their effective use in biological experiments, although solubility could presumably be increased by introduction of hydrophilic groups into the molecules.

The present invention provides oligonucleotide analog compounds, compositions comprising such compounds, intermediates for preparing such compounds and methods for synthesizing such novel stable, nuclease resistant, target specific, lipid soluble oligonucleotide analogs.

SUMMARY OF THE INVENTION

The present invention provides nucleotide analog compounds comprising oligonucleoside sequences of from about 6 to about 200 bases having a three atom internucleoside linkage. The three atom internucleoside linkage of such oligonucleoside sequences has the formula:

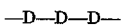

where each D is independently CHR, oxygen or NR$^6$, wherein R is independently hydrogen, OH, SH or NH$_2$, R$^6$ is hydrogen or C$_1$–C$_2$ alkyl, with the proviso that only one D is oxygen or NR$^6$.

In a preferred embodiment, the oligonucleoside sequences comprise bases selected from the group consisting of adenine, cytosine, guanine, uracil, thymine and modifications thereof.

More particularly, compounds of the present invention comprise oligonucleoside sequences of Formula I:

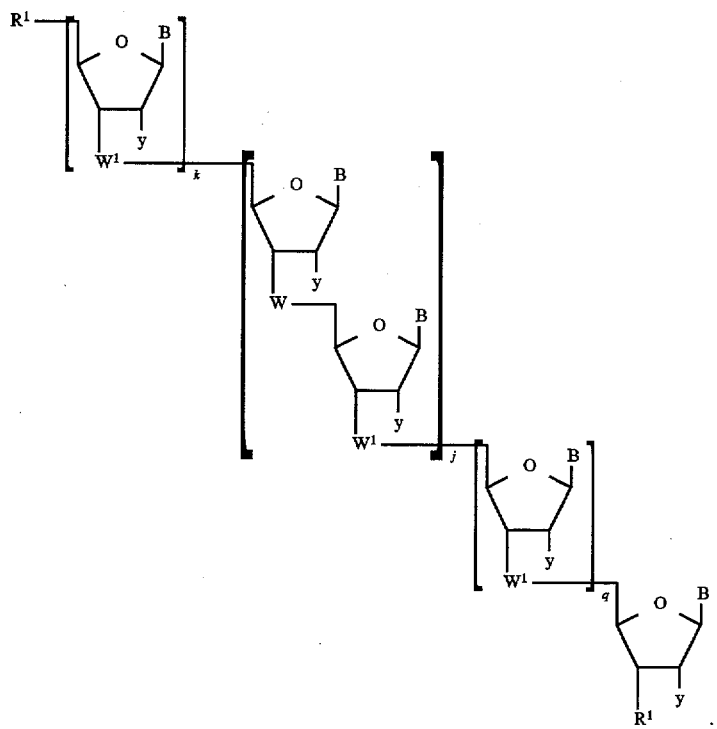

I where W is —D—D—D— wherein each D is independently CHR, oxygen or $NR^6$, wherein R is independently hydrogen OH, SH or $NH_2$, $R^6$ is hydrogen or $C_1$-$C_2$ alkyl with the proviso that only one D is oxygen or $NR^6$;

each W' is independently W or

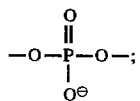

each $R^1$ is independently OH, SH, $NR^2R^3$ wherein $R^2$ and $R^3$ are independently hydrogen or $C_1$-$C_6$ alkyl or $NHR^4$ wherein $R^4$ is $C_1$-$C_{12}$ acyl;

each y is independently H or OH;

each B is independently adenine, cytosine, guanine, thymine, uracil or a modification thereof;

j is an integer from 1 to about 200;

k is 0 or an integer from 1 to about 197; and q is 0 or an integer from 1 to about 197, with the proviso that the sum of j+k+q is from about 4 to about 200.

The compounds of the present invention comprise oligonucleotide or oligonucleoside sequences optionally having a diol at either or both termini.

Preferred diols are 1,2-diols (glycols). Representative glycols are polyalkyleneglycols, preferably polyethyleneglycols or polypropyleneglycols. Preferred glycols are tetraethyleneglycol and hexaethyleneglycol. Suitable diols may also include polyols that have all but two hydroxyls blocked.

Where the compounds of the present invention are oligonucleoside sequences having a diol at either or both termini, the compounds of the present invention have Formula II:

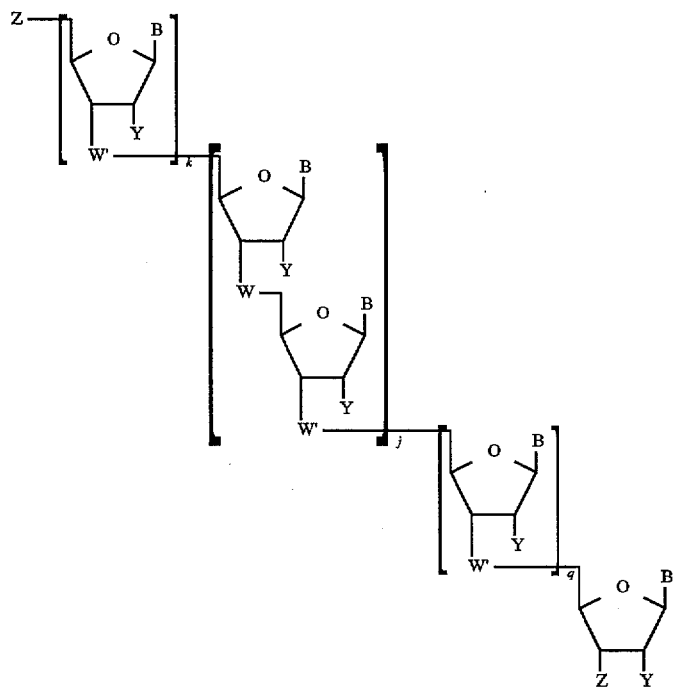

II where each Z is independently $R^1$ or

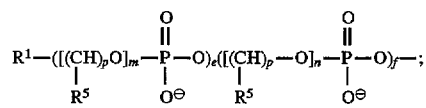

where each $R^1$ is independently OH, SH, $NHR^2R^3$ wherein $R^2$ and $R^3$ are independently hydrogen, or $C_1$–$C_6$ alkyl, or $NHR^4$ wherein $R^4$ is $C_1$–$C_{12}$ acyl;

each $R^5$ is independently hydrogen or $C_1$–$C_{12}$ alkyl;

each of W, W', Y, B, j, k, and q is as defined above;

each e and f is independently 0 to 50 with the proviso that at least one of e and f be at least 1;

each m and n is independently 1 to 200; and each p is independently 2 to 4.

In a preferred embodiment, the sum of j+k+q is from about 9 to about 50 bases, more preferably from about 12 to about 25 and most preferably from about 15 to about 18. In this embodiment, compounds of this invention comprise oligonucleotides of the formula:

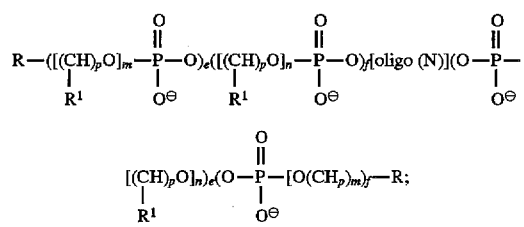

where R is OH, SH, $NR^2R^3$ wherein $R^2$ and $R^3$ are independently hydrogen or $C_1$–$C_6$ alkyl, or $NHR^4$ wherein $R^4$ is $C_1$–$C_{12}$ acyl;

$R^1$ is hydrogen or $C_1$–$C_{12}$ alkyl; oligo (N) is a native or modified oligonucleotide sequence of from about 9 to about 200 bases; each e and f is independently 0 to 50, with the proviso that at least one of e and f be at least 1;

each m and n is independently 1 to 200; and each p is independently 2 to 4.

In a preferred embodiment, the oligonucleotide contains, in a homopolymer or heteropolymer sequence, any combination of dA, dC, dG, T.

Where the glycol is polyethyleneglycol, the compounds of this embodiment comprise oligonucleotides of the formula:

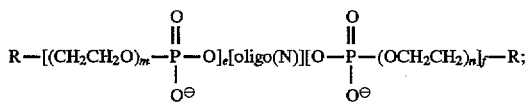

where R is OH, SH, $NR^2R^3$ wherein $R^2$ and $R^3$ are independently hydrogen or $C_1$–$C_6$ alkyl, or $NHR^4$ wherein $R^4$ is $C_1$–$C_{12}$ acyl;

oligo N is an oligonucleotide sequence of from about 9 to about 50 bases;

e and f are independently 0 to 50, with the proviso that at least one of e and f be at least 1;

m and n are independently 0 to 200 with the proviso that at least one of m and n be 1 to 200.

The oligonucleotides of the present invention can include known internucleoside linking groups such as phosphodiester, silyl and other well known linking groups providing they contain an effective amount of the —D—D—D— linking groups of the present invention and/or diol terminating groups of the present invention.

The present invention is also directed to nucleoside dimers of the formula:

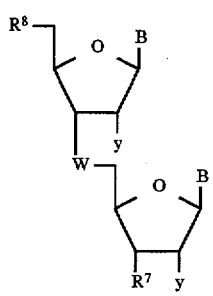

where W is —D—D—D— wherein each D is independently CHR, oxygen or $NR^6$ wherein R is independently hydrogen, OH, SH or $NH_2$, $R^6$ is hydrogen or $C_1$–$C_2$ alkyl, with the proviso that only one D is oxygen or $NR^6$;

each B is independently adenine, cytosine, guanine, thymine, uracil or a modification thereof;

$R^7$ is OH, t-butyldimethylsilyloxy or a phosphoramidite and $R^8$ is OH, a protecting group or t-butyldimethylsilyloxy.

The present invention further provides a method of inhibiting nuclease degradation of compounds comprising oligonucleoside sequences. This method comprises attaching a diol to either the 5', the 3' terminus or both termini of said compound. The diols are attached to the 5' and/or the 3' terminus by reacting the oligonucleotide compounds with an alkoxytrityldiolcyanophosphine, preferably a dimethoxytritylglycolcyanophosphine or a monomethoxytritylglycolcyanophosphine.

The present invention further provides a method of inhibiting nuclease degradation of native or modified nucleotide compounds comprising preparing oligonucleoside sequences of from about 6 to about 200 bases having a three atom internucleoside linkage having the formula —D—D—D— as defined herein.

The present invention also provides compositions useful in inhibiting gene expression comprising compounds comprising oligonucleoside sequences of from about 6 to about 200 bases having a three atom internucleoside linkage as defined herein and a physiologically acceptable carrier. The compound may have a diol at either or both termini. Preferred diols are polyethyleneglycols.

The present invention further provides a method of inhibiting gene expression comprising administering to a mammal in need of such treatment an effective amount of a compound comprising an oligonucleoside sequence from about 6 to about 200 bases having a three atom internucleoside linkage as defined herein. The compounds may have a diol at either or both termini. Preferred diols are polyetheleyeneglycols.

DETAILED DESCRIPTION OF THE INVENTION

Figure 1:
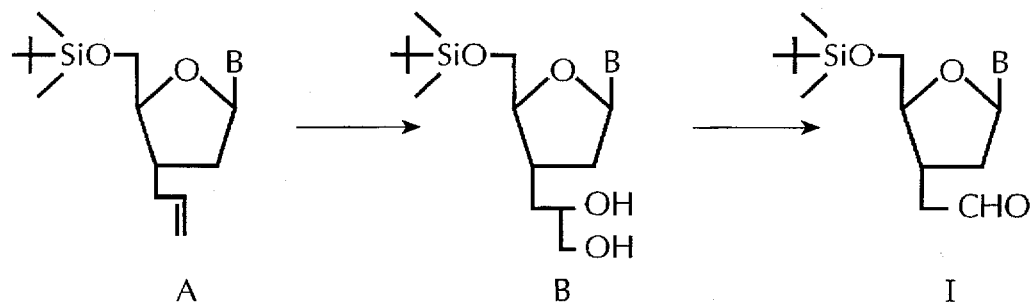
FIG. 1a depicts a synthetic pathway for preparing a nucleoside aldehyde (Compound I).
FIG. 1b depicts a synthetic pathway for preparing a phosphonium iodide nucleoside (Compound II).
Figure 1:
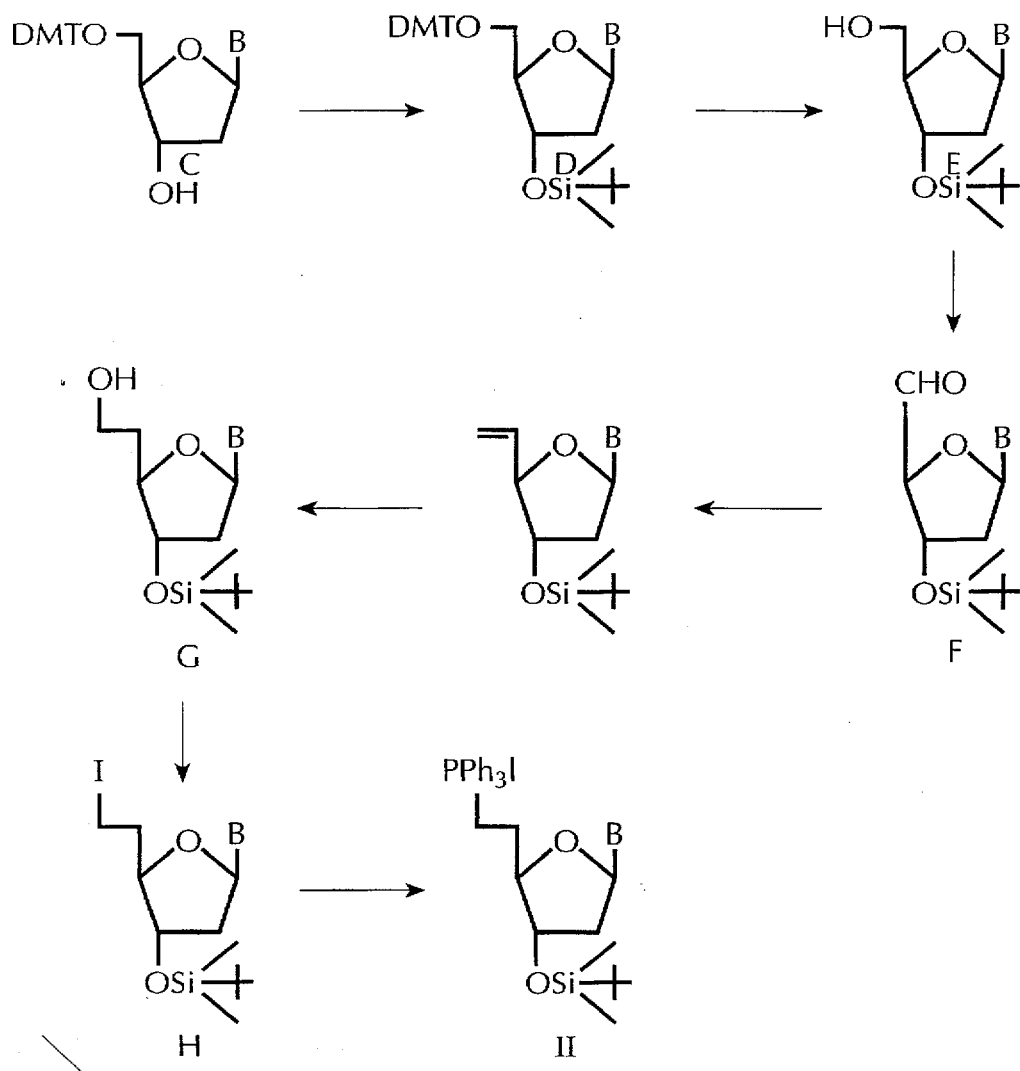

The compounds of the present invention are generally oligonucleotide or oligonucleoside sequences that are resistant to nuclease degradation.

As used herein, "nucleoside" refers to a combination of a purine or pyrimidine base with a five-carbon sugar (pentose).

As used herein, "nucleotide" refers to a phosphoric acid ester of a nucleoside.

As used herein, "oligonucleotide" refers to polynucleotides having only phosphodiester internucleoside linkages, e.g. "native" DNA or RNA.

Exemplary nucleosides are adenosine(A), guanosine(G), cytidine(C), uridine(U), deoxyadenosine (dA), deoxyguanosine(dG), deoxycytidine(dC) and thymidine(T).

The compounds of the present invention comprise oligonucleoside sequences of from about 6 to about 200 bases having a phosphodiester or a three atom internucleoside linkage. The three atom internucleoside linkage (—D—D—D—) contains 1) three carbon atoms, 2) two carbon atoms and one oxygen atom or 3) two carbon atoms and one nitrogen atom.

The oligonucleoside sequences are sequences of native or modified nucleosides. As used herein, the phrase "internucleoside linkage" refers to atoms and molecules forming a bridge between the sugar moiety carbon atom at position 3 of one native or modified nucleoside and the sugar moiety carbon atom at position 5 of an adjacent such nucleoside. The sugar moiety may be either a ribose or a deoxyribose moiety or an analog thereof. Thus, the nucleosides include A, C, G, U, dA, dC, dG, T or modifications thereof as for example 5-bromo or 5-iodouracil, 5-methyl cytosine, isocytosine (2-amino-4-oxopyrimidine), isoguanine (2-oxo-6-aminopurine), inosine (6-oxopurine), 5-vinyluracil and 5-vinylcytosine.

The three atom internucleoside linkage has the formula:

—D—D—D— where each D is independently CHR, oxygen or $NR^6$, wherein R is independently hydrogen, OH, SH or $NH_2$, oxygen, $R^6$ is hydrogen or $C_1$–$C_2$ alkyl, with the proviso that only one D is oxygen or $NR^6$.

The compounds of the present invention comprise oligonucleoside sequences of Formula I:

I

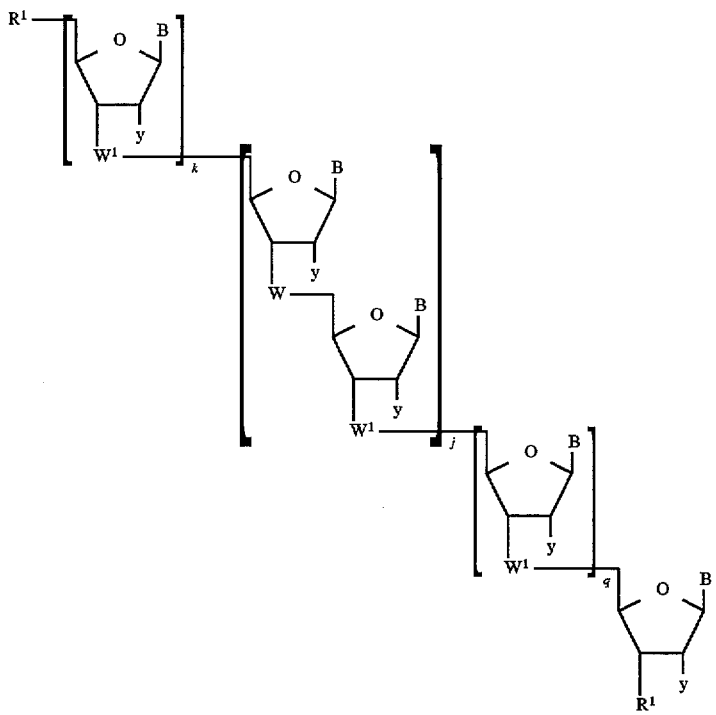

where W is —D—D—D— wherein each D is independently CHR, oxygen or $NR^6$, wherein R is independently hydrogen, OH, SH or $NH_2$, $R^6$ is hydrogen or $C_1$–$C_2$ alkyl, with the proviso that only one D is oxygen or $NR^6$;

each W' is independently W or

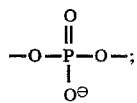

each $R^1$ is independently OH, SH, $NR^2R^3$ wherein $R^2$ and $R^3$ are independently hydrogen or $C_1$–$C_6$ alkyl or $NHR^4$ wherein $R^4$ is $C_1$–$C_{12}$ acyl;

each y is independently H or OH;

each B is independently adenine, cytosine, guanine, thymine, uracil or a modification thereof;

j is an integer from 1 to about 200;

k is O or an integer from 1 to about 197; and q is O or an integer from 1 to about 197, with the proviso that the sum of j+k+q is from about 4 to about 200.

In a preferred embodiment, the sum of j+k+q is from about 9 to about 50. In a more preferred embodiment, the sum of j+k+q is from about 12 to about 25 and, more preferably from about 15 to about 18.

The compounds of the present invention may have a diol at either or both termini. Preferred diols are glycols, also known as 1,2-diols, which contain two hydroxyl groups on adjacent carbons. Preferred glycols are polyalkyleneglycols. The term "alkylene" as used herein refers to linear and branched chain radicals having 2 to 4 carbon atoms which may be optionally substituted as herein defined. Representative of such radicals are ethylene, propylene, isobutylene, and the like. Preferred polyalkyleneglycols are polyethyleneglycols such as hexaethyleneglycol and tetraethyleneglycol. Suitable diols may also include polyols that have all but two hydroxyls blocked.

The diols are attached to either the 5', the 3' or both termini of the oligonucleosides via phosphodiester linkages. In one embodiment, the diols are attached to only one terminus of an oligonucleoside sequence.

The terminal diol is linked to a moiety selected from the group consisting of hydroxyl (OH), sulfhydryl (SH), amino ($NH_2$), alkylamino (NH-alkyl), dialkylamino (N[alkyl]$_2$) and amido (NH[acyl]).

Where glycols are present at either or both termini, the compounds of the present invention comprise oligonucleoside sequences of Formula II:

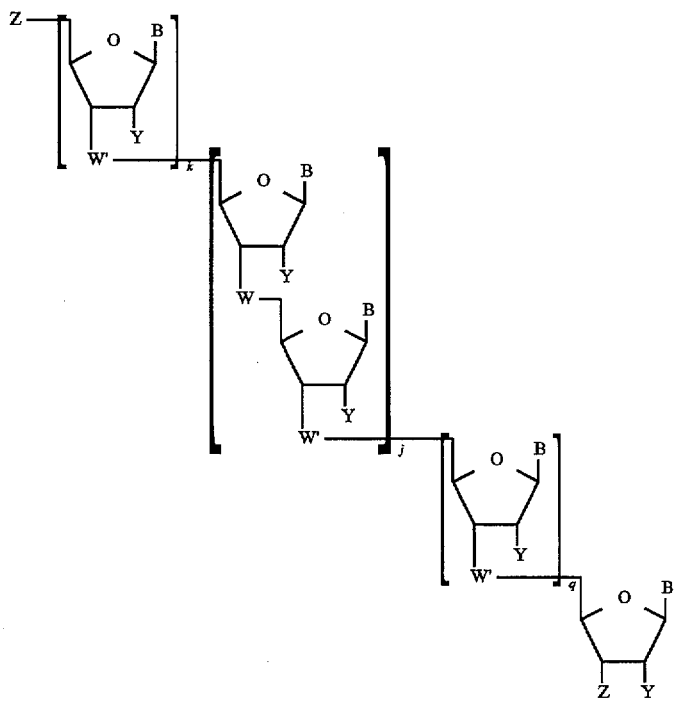

II where each Z is independently $R^1$ or

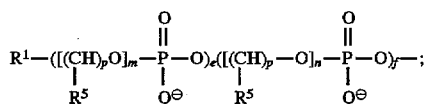

where each $R^1$ is independently OH, SH, $NHR^2R^3$ wherein $R^2$ and $R^3$ are independently hydrogen or $C_1$–$C_6$ alkyl, or $NHR^4$ wherein $R^4$ is $C_1$–$C_{12}$ acyl;

each $R^5$ is independently hydrogen or $C_1$–$C_{12}$ alkyl;

each of W, W', Y, B, j, k, and q is as defined above;

each e and f is independently 0 to 50, with the proviso that at least one of e and f be at least 1;

each m and n is independently 1 to 200; and each p is independently 2 to 4.

In a preferred embodiment, m and n are independently 1 to 6 and the sum of j+k+q is from about 9 to about 50. In a more preferred embodiment, the sum of j+k+q is from about 12 to 25, more preferably from about 15 to about 18.

In another preferred embodiment, the compounds of the present invention comprise oligonucleotide sequences of from about 9 to about 200 bases having a diol at either or both termini. In yet another preferred embodiment, the compounds of the present invention comprise oligonucleotide sequences of from about 9 to about 200 bases having a (—D—D—D—) linkage of the present invention.

Preferred diols are glycols, also known as 1,2-diols, which contain two hydroxyl groups on adjacent carbons. Preferred glycols are polyalkyleneglycols. The term "alkylene" as used herein refers to linear and branched chain radicals having 2 to 4 carbon atoms which may be optionally substituted as herein defined. Representative of such radicals are ethylene, propylene, butylene and the like. Preferred polyalkyleneglycols are polyethyleneglycols. More preferred are tetraethyleneglycol and hexaethyleneglycol.

The diols are attached to either the 5', the 3' or both termini of the oligonucleotides via phosphodiester linkages.

In one embodiment, the diols are attached to only one terminus of an oligonucleotide sequence.

The terminal diol is linked to a moiety selected from the group consisting of hydroxyl (OH), sulfhydryl (SH), amino ($NH_2$), alkylamino (NH-alkyl), dialkylamino (N[alkyl]$_2$) and amido (NH[acyl]). As used herein, "alkyl" refers to linear or branched chain radicals having 1 to 12 carbon atoms which may be optionally substituted as herein defined. Representative alkyl- and dialkylamino radicals include methyl-, ethyl-, propyl-, butyl-, pentyl-, hexyl-, dimethyl-, diethyl-, dipropyl-, dibutyl-, dipentyl- and dihexylamines and the like. As used herein, "NH(acyl)" or "amido" refers to linear or branched chain radicals having 1 to 12 carbon atoms with a terminal O=CNH$_2$ group. Representative amido radicals include methanamide, ethanamide, propanamide, butanamide, pentanamide, hexanamide, heptanamide, octanamide, nonanamide, decanamide, undecanamide and dodecanamide.

In one embodiment, the compounds of the present invention comprise oligonucleotides of the formula:

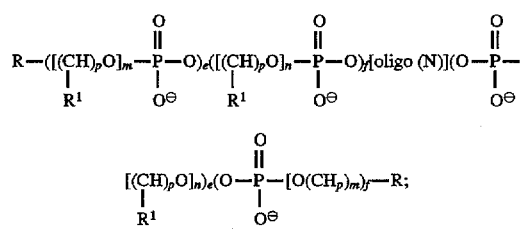

where R is OH, SH, $NR^2R^3$ wherein $R^2$ and $R^3$ are independently hydrogen or $C_1$–$C_6$ alkyl, or $NHR^4$ wherein $R^4$ is $C_1$–$C_{12}$ acyl;

$R^1$ is hydrogen or $C_1$–$C_{12}$ alkyl;

oligo (N) is a native or modified oligonucleotide sequence of from about 9 to about 200 bases;

each e and f is independently 0 to 50;

each m and n is independently 1 to 200; and each p is independently 2 to 4.

The oligonucleotide sequence is preferably a homopolymer or heteropolymer sequence containing any combination of dA, dC, dG, T or analogs thereof.

In a preferred embodiment, m and n are independently 1 to 8 and, more preferably, both m and n are 4. Preferred oligonucleotide sequences contain from about 9 to about 50 bases, more preferably about 12 to about 25 bases, and most preferably about 15 to about 18 bases.

In a preferred embodiment, the antisense compounds have polyethyalkyleneglycol at both the 5' and 3' termini and have the formula:

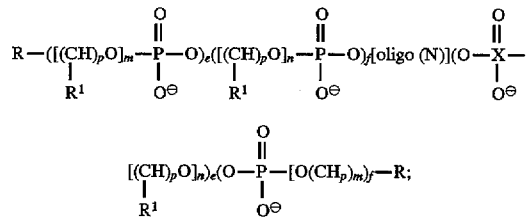

where R is OH, SH, $NR^2R^3$ wherein $R^2$ and $R^3$ are independently hydrogen or $C_1–C_6$ alkyl, or $NHR^4$ wherein $R^4$ is $C_1–C_{12}$ acyl;

$R^1$ is hydrogen or $C_1–C_{12}$ alkyl;

oligo (N) is a native or modified oligonucleotide sequence of from about 9 to about 200 bases;

each e and f is independently 1 to 50;

each m and n is independently 1 to 200; and each p is independently 2 to 4.

Where the glycol is polyethyleneglycol, the compounds of this embodiment comprise oligonucleotides of the formula:

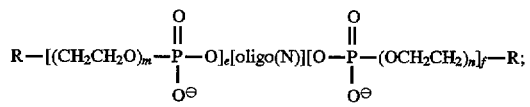

where R is OH, SH, $NR^2R^3$ wherein $R^2$ and $R^3$ are independently hydrogen or $C_1–C_6$ alkyl, or $NHR^4$ wherein $R^4$ is $C_1–C_{12}$ acyl;

oligo N is an oligonucleotide sequence of from about 9 to about 50 bases; and e, f, m and n are each independently 1 to 50.

In a preferred embodiment, the oligonucleotide contains, in a homopolymer or heteropolymer sequence, any combination of dA, dC, dG, T.

In other preferred embodiments, the polyethyleneglycol is tetraethyleneglycol (TEG) and both m and n are 4 or hexaethyleneglycol and both m and n are 6.

The compounds of the present invention are useful as antisense agents. Antisense agents hybridize with a complementary nucleotide sequence in a target nucleic acid to inhibit the translational or transcriptional function of said target nucleic acid. The target nucleic acid may be either RNA or DNA.

Antisense compounds of the present invention comprise oligonucleoside sequences of from about 6 to about 200 bases having homopolymer or heteropolymer sequences comprising bases selected from the group consisting of adenine (A), cytosine (C), guanine (G), uracil (U), thymine (T) and modifications of these bases. Particular sequences are selected on the basis of their desired target. The sequence selected hybridizes with the target nucleic acid. Exemplary targets include the MYC oncogene, the RAS oncogene, and vital nucleic acids.

The compounds of the present invention can be prepared by the following procedures:

A. Compounds having a three carbon internucleoside linkage

Oligonucleosides connected by a three-carbon internucleoside linkage are synthesized by reacting nucleosides having aldehyde and ylide functionalities at 3' and 6' positions respectively under Wittig conditions.

The syntheses of a nucleoside aldehyde and a phosphonium iodide nucleoside from commercially available compounds are illustrated in FIG. 1a and 1b, respectively. The aldehyde (Compound I from FIG. 1a) is synthesized from the known 3'-allyl-3'-deoxy-5'-O-tert-butyldimethylsilyl-3'-thymidine (Compound A, FIG. 1). The allyl compound is regioselectively oxidized with a catalytic amount of osmium tetroxide and N-methylmorpholine oxide as a cooxidant. The resultant diol (Compound B, FIG. 1a) is cleaved with sodium periodate to give the aldehyde in almost quantitative yield.

The synthesis of the phosphonium iodide nucleoside (Compound II, FIG. 1b) follows from a commercially available 5'-tritylated nucleoside (Compound C, FIG. 1b). The tritylated nucleoside is silylated at the 3' position with tert-butyldimethylsilyl chloride and the trityl group removed under acidic conditions with high efficiency. The resultant primary hydroxyl (Compound E, FIG. 1b) is oxidized under Swern conditions to give the aldehyde (Compound F, FIG. 1b). The crude aldehyde is immediately reacted with the ylide derived from methyltriphenylphosphonium bromide to give a 4'-vinyl- 4'-deoxy-3'-tert-butyldimethylsilyl nucleoside in good yield. The vinyl compound is regioselectively hydroborated to give a primary alcohol (Compound G, FIG. 1b) in good yield. The primary alcohol in turn is converted to the corresponding iodide (Compound H, FIG. 1b) using triphenylphosphine-iodine in the presence of imidazole in excellent yield. Finally, the iodide is transformed to the desired phosphonium iodide nucleoside using triphenylphosphine in acetonitrile.

Figure 2:
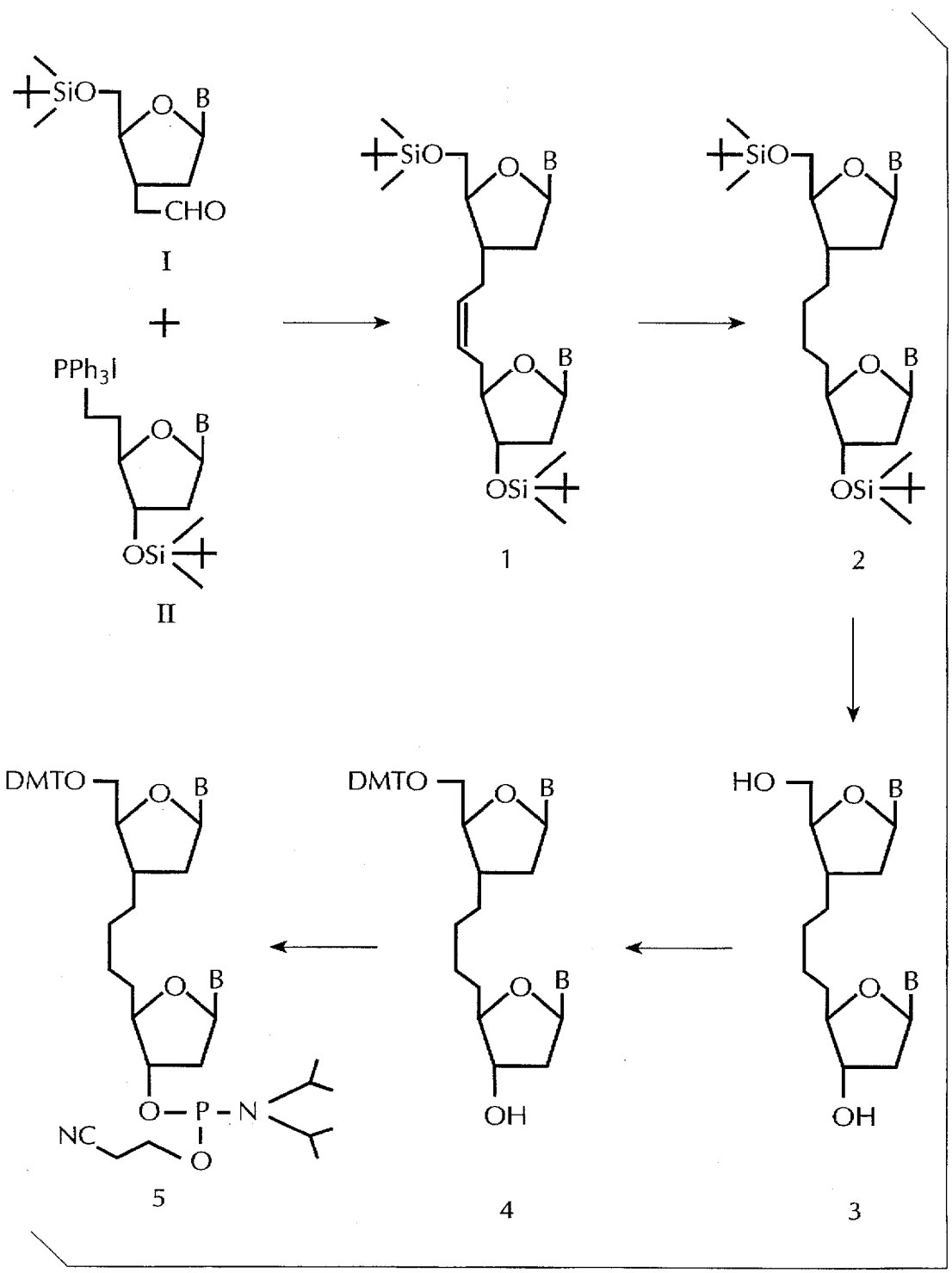
FIG. 2 depicts a synthetic pathway for preparing nucleoside dimers connected by a 3 carbon internucleoside linkage utilizing the aldehyde nucleoside and the phosphonium iodide nucleoside of FIGS. 1a and 1b respectively.

A ylide is prepared from the phosphonium iodide nucleoside using potassium tert-butoxide as a base and immediately reacted with the aldehyde to give a Wittig product (Compound 1, FIG. 2) in good yield. The Wittig product is regioselectively hydrogenated with 10% palladium on carbon (10% Pd—C) with hydrogen at atmospheric pressure in quantitative yield to saturate the double bond of the linkage. The saturated compound (Compound 2, FIG. 2) is desilylated with tetrabutylammonium fluoride to give the diol (Compound 3, FIG. 2). The 5'-primary hydroxyl of the diol is then regioselectively protected with dimethoxytrityl chloride and the resultant 3'-hydroxyl (Compound 4, FIG. 2) is converted to a phosphoramidite (Compound 5, FIG. 2) with 2-cyanoethyl-N,N-diisopropylchlorophosphoramidite.

The nucleoside dimers or higher oligomers with trialkylsilyloxy protecting groups are conjugated to form oligonucleotides of any desired length. Upon completion of chain elongation, the oligomers are deprotected by standard methods. For further chain length extension in a solid phase synthesizer in which the oligomers are connected by phosphate linkages, the terminal 5'- and 3'-hydroxyl groups of the oligomers are appropriately functionalized, respectively with tritylating reagents such as dimethoxytritylchloride and phosphoramidite.

B. Compounds having a two carbon-one oxygen atom internucleoside linkage

Oligonucleoside sequences having a two carbon-one oxygen atom internucleoside linkage are synthesized by reacting 3'-silylated, 5'-toluenesulfonyl nucleoside with a 5'-protected nucleoside.

A 3'-acetyl-5'-aldehyde nucleoside is prepared from a commercially available 3'-acetyl-nucleoside using standard methods well known to those of skill in the art. The 3'-acetyl-5'-aldehyde nucleoside is then converted to a 3'-acetyl-5'-carbomethoxymethylene nucleoside using a modified Wittig reaction.

The 5'-methylene side chain is reduced with sodium borohydride in alcohol, preferably isopropanol, followed by deprotection of the 3'-acetyl group with sodium methoxide in an alcohol, preferably methanol. The 3'-hydroxy is then protected with a silyl group. In a preferred embodiment the silyl group is a t-butyldimethylsilyl group.

The 3'-silyl-5'-carbomethoxymethyl nucleoside is then further reduced to a 3'-O-silyl-5'-deoxy-3'-(2"-ethanol) derivative of the nucleoside with diisobutyl aluminum hydride (DIBAL) in tetrahydrofuran (THF). The 5'-ethanol group is converted to a p-toluenesulfonyl group with p-toluene sulfonyl chloride in pyridine. The exocyclic amino group of the base moiety of the 5'-p-toluenesulfonyl nucleoside is optionally protected by methods well known and readily apparent to those of skill in the art. A preferred protecting group for the exocyclic amino groups of adenine and cytosine is the benzoyl moiety. A preferred protecting group for the exocyclic amino group of guanine is the isobutyl moiety. Guanine may also be protected at the $O^6$ position.

The 3'-O-silyl-5'-O-p-toluenesulfonyl nucleoside is then reacted with a 5'-protected nucleoside to form a 3'-O-silyl-5'-protected nucleoside dimer with a two carbon-one oxygen atom internucleoside linkage. The 5'-O-protecting group is preferably a trityl and, more preferably a dimethoxytrityl. The 3'-O-silyl-5'-O-protected nucleoside is optionally protected at the exocyclic amino groups of the nucleoside base moiety.

The nucleoside dimers are deprotected and rederivatized at the 3'-carbon atom position with a cyanophosphine reagent, preferably 2-cyanoethoxydiisopropylaminophosphine for use in a phosphoramidite solid phase synthesis method of chain elongation. Gait, supra.

The nucleoside dimers or higher oligomers with trialkylsilyloxy protecting groups are conjugated to form oligonucleosides of any desired length. Upon completion of chain elongation, the oligomers are deprotected by standard methods. For further chain length extension in a solid phase synthesizer in which the oligomers are connected by phosphate linkages, the terminal 5' and 3' hydroxyl groups of the oligomers are appropriately functionalized, respectively with tritylating reagents such as dimethoxytritylchloride and phosphoramidite.

C. Compounds having a two carbon-one nitrogen atom internucleoside linkage

Figure 4:
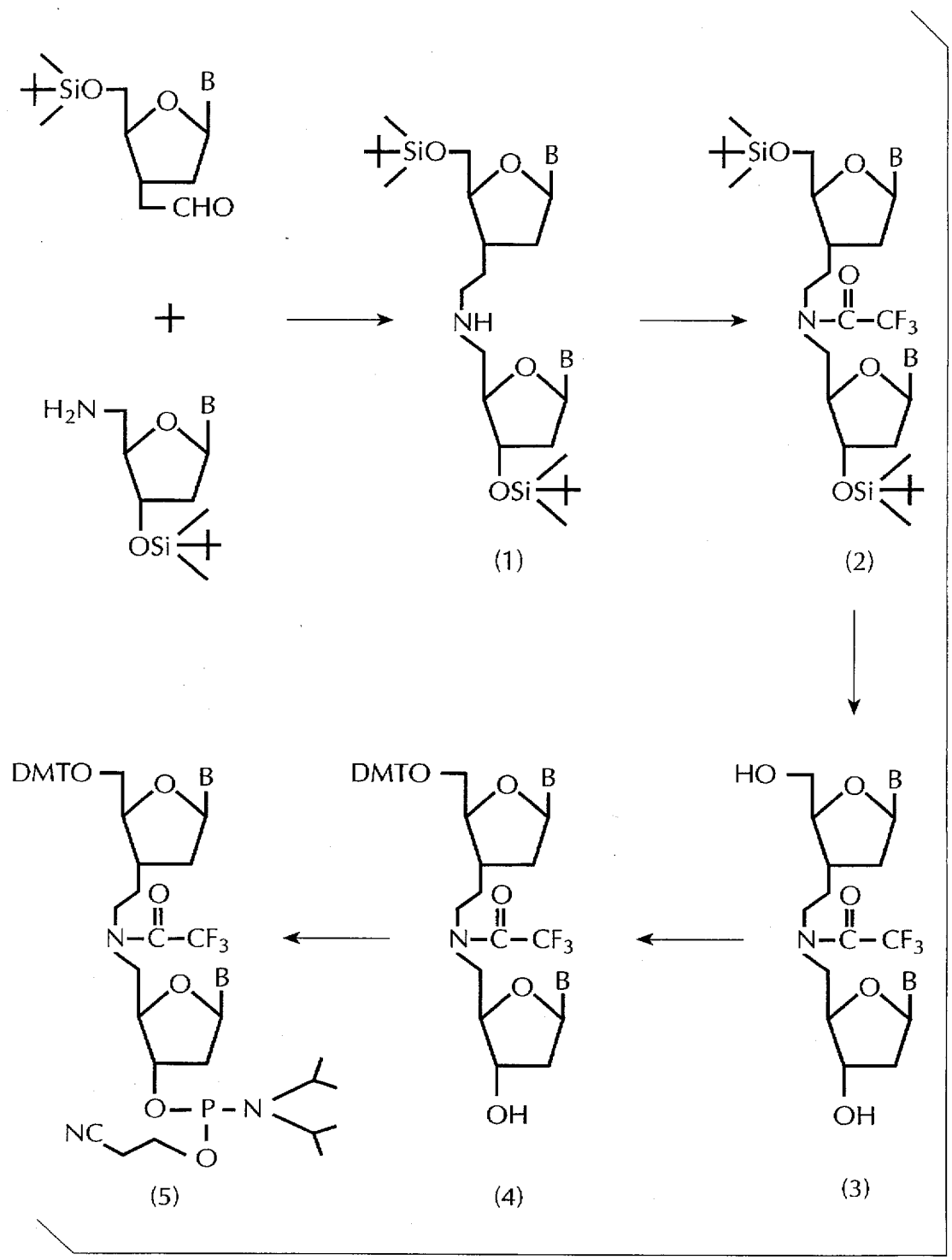
FIG. 4 depicts a synthetic pathway for preparing a nucleoside dimer connected by a two carbon-one nitrogen atom internucleoside linkage of the form 3'-C—C—N-5'. Dimers are synthesized by reacting nucleosides that contain aldehydes (CHO) with nucleosides that contain amine functionalities ($NH_2$) under reductive conditions.

Oligonucleoside sequences connected by a two carbon-one nitrogen atom internucleoside linkage of the form C—C—N are synthesized by reacting nucleosides that contain aldehydes with nucleosides that contain amine functionalities under reductive conditions as illustrated in FIG. 4.

Both the aldehyde and the amine compounds are prepared from commercially available compounds. The aldehyde is prepared from 3'-allyl-3'-deoxy-5'-O-tert-butyldimethylsilyl thymidine. The allyl compound is regioselectively oxidized with a catalytic amount of osmium tetroxide in the presence of N-methyl morpholine,N-oxide as a cooxidant to give the diol. The diol is, in turn, oxidized with sodium periodate to give the aldehyde in almost quantitative yield.

The amine compound is synthesized from commercially available nucleosides. In a typical procedure, the primary hydroxyl group of a nucleoside is regioselectively transformed into a tosylate group with p-toluene sulfonyl chloride and then converted into an iodide. The 3'-hydroxy of the iodide intermediate is protected with tert-butyldimethylsilyl chloride and the azido group introduced by reacting with sodium azide. The azido functionality is efficiently converted to the required amine by reduction using 10% palladium on carbon under a hydrogen atmosphere or Raney Nickel reduction conditions.

The amine and the aldehyde are coupled (reductive amination) in the presence of sodium cyanoborohydride under buffered conditions. The oligonucleoside dimer with a C—C—N internucleoside linkage is formed in good yield. The oligonucleoside is reacted with trifluoroacetic anhydride-triethylamine, to protect the secondary aliphatic nitrogen. The protected oligonucleoside is desilylated with tetrabutylammonium fluoride and the primary hydroxyl group of the resultant diol is selectively protected with dimethoxytrityl chloride. The remaining secondary hydroxyl is transformed to the required phosphoramidite by reacting with 2-cyanoethyl-N,N-diisopropylchlorophosphoramidite.

Figure 5:
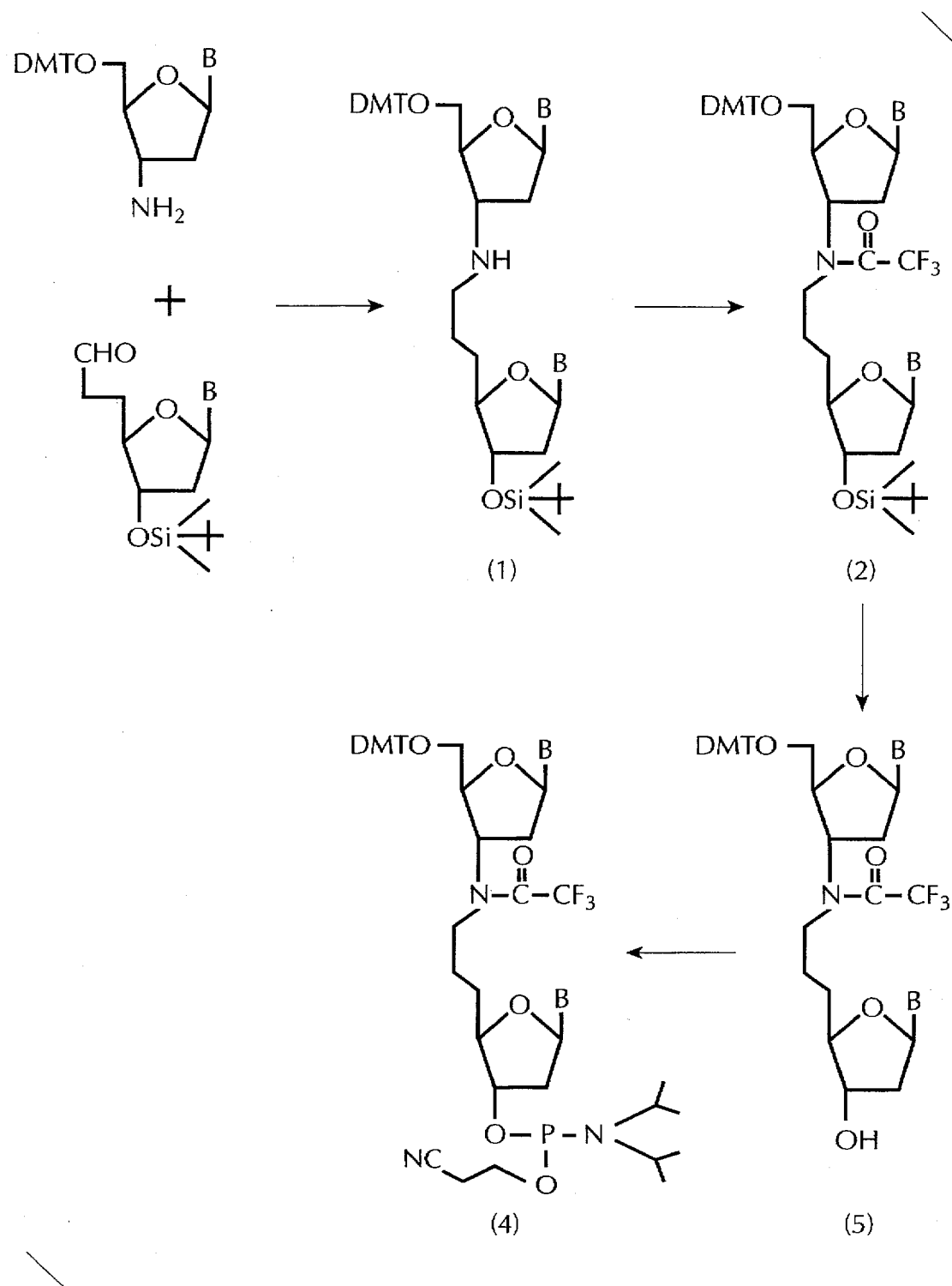
FIG. 5 depicts a synthetic pathway for preparing a nucleoside dimer connected by a two carbon-one nitrogen atom internucleoside linkage of the form 3'-N—C—C-5'. Dimers are synthesized by reacting nucleosides having aldehyde and amine functionalities under reductive conditions.

Oligonucleosides connected by two carbon-one nitrogen atom internucleoside linkage of the form N—C—C are synthesized by reacting nucleosides having aldehyde and amine functionalities at 3'- and 5'- positions, respectively, under reductive conditions as illustrated in FIG. 5.

The amine and the aldehyde components are synthesized from commercially available compounds. The amine is synthesized from 3-azido-3-deoxy thymidine (AZT). The primary hydroxyl group of AZT is protected with dimethoxytritylchloride and the resultant azide regioselectively transformed to the required amine with 10% palladium on carbon in the presence of a hydrogen atmosphere or using Raney Nickel.

The aldehyde is synthesized from commercially available 5'-O-dimethoxytritylthymidine. The tritylated thymidine is silylated with tert-butyldimethylsilyl chloride and the trityl group is removed under acidic conditions. The resultant primary hydroxyl group is oxidized under Swern conditions to give the aldehyde. The aldehyde is not isolated but immediately reacted with (carbethoxymethylene) triphenylphosphorane to give the unsaturated ester. The unsaturated ester is regioselectively hydrogenated with 10% palladium on carbon to give a saturated ester in quantitative yield. The saturated ester in turn is converted to the required aldehyde with diisobutyl aluminum hydride (DIBAL-H) in a highly selective manner.

The amine and the aldehyde are coupled in the presence of sodium cyanoborohydride under buffered reductive amination conditions. The N—C—C internucleoside linkage is obtained in good yield. The secondary aliphatic nitrogen of the oligonucleoside is protected with trifluoroacetic anhydride and triethylamine. The protected dimer or higher oligonucleoside sequence is desilylated and the resultant hydroxyl converted to phosphoramidite with 2-cyanoethyl-N,N-diisopropyl-chlorophosphoramidite.

The nucleoside dimers or higher oligomers with trialkylsiloxyl protecting groups are conjugated to form oligonucleosides of any desired length. Upon completion of chain elongation, the oligomers are desilylated by standard methods. For further chain length extension in a solid phase synthesizer in which the oligomers are connected by phosphate linkages, the terminal 5' and 3' hydroxyl groups of the oligomers are appropriately functionalized, respectively with tritylating reagents such as dimethoxytritylchloride and phosphoramidite.

D. Compounds having a diol at either or both termini

Where desired, diols are attached to either or both termini by a modification of the solid phase phosphoramidite method. *Oligonucleotide Synthesis: A Practical Approach*, ed. by M. J. Gait, pages 35–81, IRL Press, Washington, D.C. (1984).

In accordance with our modification of the solid phase method, a diol is introduced at one, or both, terminal(s) of the oligonucleotide by a procedure in which the diol is reacted with an alkoxytrityl compound to form a tritylated diol. The diol is preferably a glycol, more preferably, a polyalkyleneglycol. The alkoxytrityl reagent is preferably monomethoxytrityl chloride or dimethoxytrityl chloride and, most preferably dimethoxytrityl chloride. The tritylated diols are then reacted with a cyanophosphine reagent to form a trityldiolcyanophosphine compound, which compound is used as a phosphoramidite reagent (hereinafter referred to as a "diol phosphoramidite reagent") in the solid phase synthesis of the compounds of the present invention.

The initial step in solid phase synthesis is attachment of a nucleoside to a solid support, preferably a controlled pore glass (CPG) support. The nucleoside is preferably attached to the CPG via a succinate linkage at the 3'-hydroxyl position of the nucleoside. Other means of attaching nucleosides to solid supports are known and readily apparent to those of skill in the oligonucleotide synthesis art. Alternatively, in order to introduce a diol at the 3' terminal, a diol phosphoramidite reagent can be attached to the solid support prior to addition of the first nucleoside. The diol phosphoramidite reagent is attached to the solid support using succinate or other linkages in a manner analogous to methods used for nucleoside attachment. Means of modifying such methods for use with diol phosphoramidite reagents will be readily apparent to those of skill in the art. Any number of diols can be placed on the solid support prior to addition of the first nucleoside. Preferably from 1 to about 50 diols are used. Where diols are attached only to the 5' terminus, no diols are placed on the solid support.

Following attachment of the first nucleoside or the diol(s) to the solid support, chain elongation occurs via the sequential steps of removing the 5'-hydroxyl protecting group (a functionalized trityl group), activating the 5'-hydroxyl group in the presence of a phosphoramidite reagent, i.e., a 5'-trityl nucleoside, 3'-phosphoramidite, capping the unreacted nucleosides and oxidizing the phosphorous linkage.

The protecting group at the 5'-hydroxyl position of the attached nucleosides is removed with acid, preferably trichloroacetic acid.

Activating reagents that can be used in accordance with this method are well known to those of skill in the art. Preferred activating reagents are tetrazole and activator gold (Beckman Instr. Inc., Palo Alto, Calif.).

The activation step occurs in the presence of the added nucleoside phosphoramidite reagent or diol phosphoramidite reagent, which latter reagent replaces the nucleoside phosphoramidite reagent of conventional synthetic methods when diol is added to the terminal(s) of the polynucleotide. Unreacted chains are terminated or capped with capping reagents such as acetic anhydride and N-methyl imidazole.

The labile trivalent phosphorus linkage is oxidized, preferably with iodine, to the stable, pentavalent phosphodiester linkage of the oligonucleotide.

After the desired oligonucleotide chain assembly is complete, the phosphate protecting groups are removed, the chains are separated from the solid support and the base protecting groups are removed by conventional methods. Gaits, supra at 67–70.

Those skilled in the art will appreciate that other means of synthesizing oligonucleotides can be modified in an analogous manner to produce diol-terminated antisense oligonucleotides.

The compounds of the present invention are useful in treating mammals with hereditary disorders or diseases associated with altered genetic expression mechanisms. At present, attempts are underway to develop antisense therapies for use in treating vital infections such as HIV, cytomegalovirus, herpes simplex, hepatitis B, papilloma virus and picorna virus; cancers of the lung, colon, cervix, breast and ovary; inflammatory diseases; and diseases of the immune system such as acquired immunodeficiency syndrome (AIDS), hematological neoplasma and hyperproliferative disorders. Armstrong, supra at 89; Klausher, supra at 303, 304.

Compositions of the present invention useful in inhibiting gene expression comprise physiologically acceptable carriers and 1) compounds comprising oligonucleoside sequences of from about 6 to about 200 bases having an internucleoside linkage of the formula —D—D—D— as defined herein, optionally having a diol at either or both termini or 2) compounds comprising oligonucleotide sequences of from about 9 to about 200 bases having a diol at either or both termini.

Compositions of the present invention useful in inhibiting gene expression include one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include physiologically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any needed preservatives, buffers or propellants as may be required. Ophthalmic formulations, eye ointments, powders and solutions are also contemplated as being within the scope of this invention.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the lipoxygenase inhibiting compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, *Methods in Cell Biology*, Ed. by Prescott, Volume XIV, Academic Press, New York, N.Y., p. 33 et seq., (1976).

Actual dosage levels of active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided doses may be in amounts, for example, of from about 1 nanomol to about 5 micromols per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The following examples further illustrate the best mode of carrying out the invention and are not to be construed as limiting of the specification and claims in any way.

EXAMPLE 1

Preparation of 5-O'-dimethoxytrityl-3-O'-t-butyldimethylsilyl thymidine

Dimethoxytrityl thymidine (5.0 g, 9.2 mmol) and imidazole (1.2 g, 18.4 mmol) were dissolved in 15 ml of anhydrous dimethyl formamide (DMF) and added to tert-butyldimethylsilyl chloride (1.7 g, 11.5 mmol).

The reaction mixture was stirred for 4 hours at room temperature, diluted with ethyl acetate and washed with water, saturated sodium chloride and dried with sodium sulfate. A quantitative yield of the title compound was obtained.

EXAMPLE 2

Preparation of 3+-O-t-butyldimethylsilyl thymidine

5'-O-dimethoxy-3'-O-t-butyldimethylsilyl thymidine prepared according to the method of Example 1 (0.7 g, 1.1 mmol) was treated for 1 hour at room temperature with 13 ml of a 3% trichloracetic acid in methylene chloride solution. The reaction mixture was then neutralized with a 5% (w/v) sodium bicarbonate solution. The organic layer was dried with sodium sulfate. The title compound was purified by flash chromatography using a 0 to 30% gradient of ethyl acetate in methylene chloride. The yield of the reaction was 85%.

EXAMPLE 3

Preparation of 3'-O-t-butyldimethylsilyl thymidine 4'-aldehyde

To a well stirred solution of dry methylene chloride at −78° C. was added oxalyl chloride (33.0 mmol, 2.88 ml) followed by dropwise addition of DMSO (3.12 ml, 4.4 mmol). After 10 minutes, the alcohol (5.6 g, 15.7 mmol), prepared according to the method of Example 2, in 20.0 ml of $CH_2Cl_2$, was added dropwise over a period of 2 minutes and stirring was continued for 45 minutes. $Et_3N$ (8,1 ml, 58.1 mmol) was added and stirring continued for another 45 minutes. The reaction mixture was then brought to room temperature and then washed with water (2×10 ml) followed by brine (10 ml) and dried ($Na_2SO_4$). The crude aldehyde was used for the next step.

EXAMPLE 4

Preparation of 5'-vinyl-5'-deoxy-3'-t-butyldimethylsilyl deoxythymidine

To a solution of methyltriphenyl phosphonium bromide (0.7 mmol) in dry tetrahydrofuran (THF) at 0° C. was added a solution of sodium bis (trimethylsilylamide) (0.6 mmol) dropwise. After 30 minutes, a solution of the corresponding 4'-aldehyde in THF was added dropwise under nitrogen. The reaction mixture was stirred for 2 hours, diluted with ethyl acetate, washed with water, then with brine and dried ($Na_2SO_4$). The title compound was purified by flash chromatography using 20% ethyl acetate-hexane. The yield was 55–60%.

EXAMPLE 5

Preparation of 3'-O-t-butyldimethylsilyl-5'-deoxy-5'-hydroxymethyl thymidine

To a solution of 2M 2-methyl-2-butene (1.6 eq, 1.5 ml, 3 mmol) in 3 ml of anhydrous THF at 0° C., 1.6 eqs of a 1M borane-tetrahydrofuran complex (3 ml, 2 mmol) were added slowly under $N_2$.

The solution was stirred for 10 minutes followed by the addition of the vinyl thymidine, prepared according to the method of Example 4, (0.7 g, 1.9 mmol) in 5 ml of anhydrous THF. The reaction mixture was stirred for 45 minutes and placed in the refrigerator for 2 days.

Workup was done using an aqueous solution comprising 3.1 eq of 2M sodium hydroxide and 3.1 eq of 30% hydrogen peroxide (preferably adding hydrogen peroxide dropwise to the aqueous sodium hydroxide at 0° C. and stirring for 10 minutes). The solution was added slowly through an addition funnel to the reaction mixture at 0° C., stirred for i hour, removed from the ice bath, diluted with ethyl acetate, washed with water, saturated sodium chloride and dried with sodium sulfate. The title compound was purified by flash chromatography using a 20–80% gradient of ethyl acetate in hexane. The yield was 62%.

EXAMPLE 6

Preparation of 5'-iodomethyl-5'-deoxy-3'-O-t-butyldimethylsilyl thymidine

To a solution of 3'-O-t-butyldimethylsilyl-5'-deoxy-5'-hydroxymethyl thymidine prepared according to the method of Example 5 (0.3 g, 0.9 mmol) in dry acetonitrile (5 ml) and ether (3.4 ml) were added 3 eq of triphenyl phosphine (0.7 g, 2.8 mmol), 4 eq of imidazole (0.3 g, 3.7 mmol) and 2.2 eq of iodine (0.5 g, 2.8 mmol). The reaction mixture was stirred for 45 min and the solvent was evaporated. Ethyl acetate was added to the residue and the residue washed with water, saturated sodium chloride and dried with sodium sulfate. The title compound was purified by flash chromatography using a 30–50% gradient of ethyl acetate in hexane. The yield was 90%.

EXAMPLE 7

Preparation of 3'-O-t-butyldimethylsilyl-5'-deoxy-5'-thymidyl methyl phosphonium iodide To a stirred solution of 5'-iodomethyl-5'-deoxy-3'-O-t-butyldimethysilyl thymidine prepared according to the method of Example 6 was added iodide (480 mg, 1 mmol) in dry $CH_3CN$ (5 ml) and triphenylphosphine (1.57 g, 6 mmol) and the mixture refluxed for 12 hours at 90° C. The reaction was cooled and the solvent was removed. The title compound was purified by flash chromatography using 5% MeOH in $CH_2Cl_2$. The product was obtained in 95–96% yield.

EXAMPLE 8

Preparation of 5'-t-butyldimethylsilyl-3'-deoxy-3'-(1",2"-dihydroxy-3"-propyl)thymidine Osmium tetraoxide ($OsO_4$) (4 drops, 2.5 w/v %) in butanol was added to a stirred mixture of 3'-(2"-propenyl)-3'-deoxy-5'-O-t-butyldimethylsilyl thymidine prepared according to the procedure described in *J. Org. Chem.* 1989, 54:2767–2769 (C. K. Chu et al.) (183 mg, 0.5 mmol) and 4-methylmorpholine-N-oxide (53 mg, 0.45 mmol) in 5.0 ml anhydrous THF at 0° C. The reaction mixture was then quenched with 10% aqueous sodium metabisulfite (2.0 ml), stirred for 20 minutes, filtered over a pad of silica and diluted with ethyl acetate (25.0 ml). The organic phase was washed with water (5.0 ml) and brine, and then dried with $Na_2SO_4$. The solvent was evaporated and the title compound purified by flash chromatography.

EXAMPLE 9

Preparation of 5'-O-t-butyldimethylsilyl-3'-deoxy-thymid-3'yl-acetaldehyde

Sodium periodate (214 mg, 1 mmol) was added to a stirred solution of the thymidine diol prepared by the method of Example 2 (200 mg, 0.5 mmol) in THF-H$_2$O (4:1 ratio, 5.0 ml). After 1 hour, the reaction mixture was diluted with ethyl acetate (25 ml), washed with (2×5 ml), brine and dried. The title compound was purified by flash chromatography with 70% ethyl acetate in hexane.

EXAMPLE 10

Preparation of thymidine dimers with a three carbon internucleoside linkage

Figure 3:
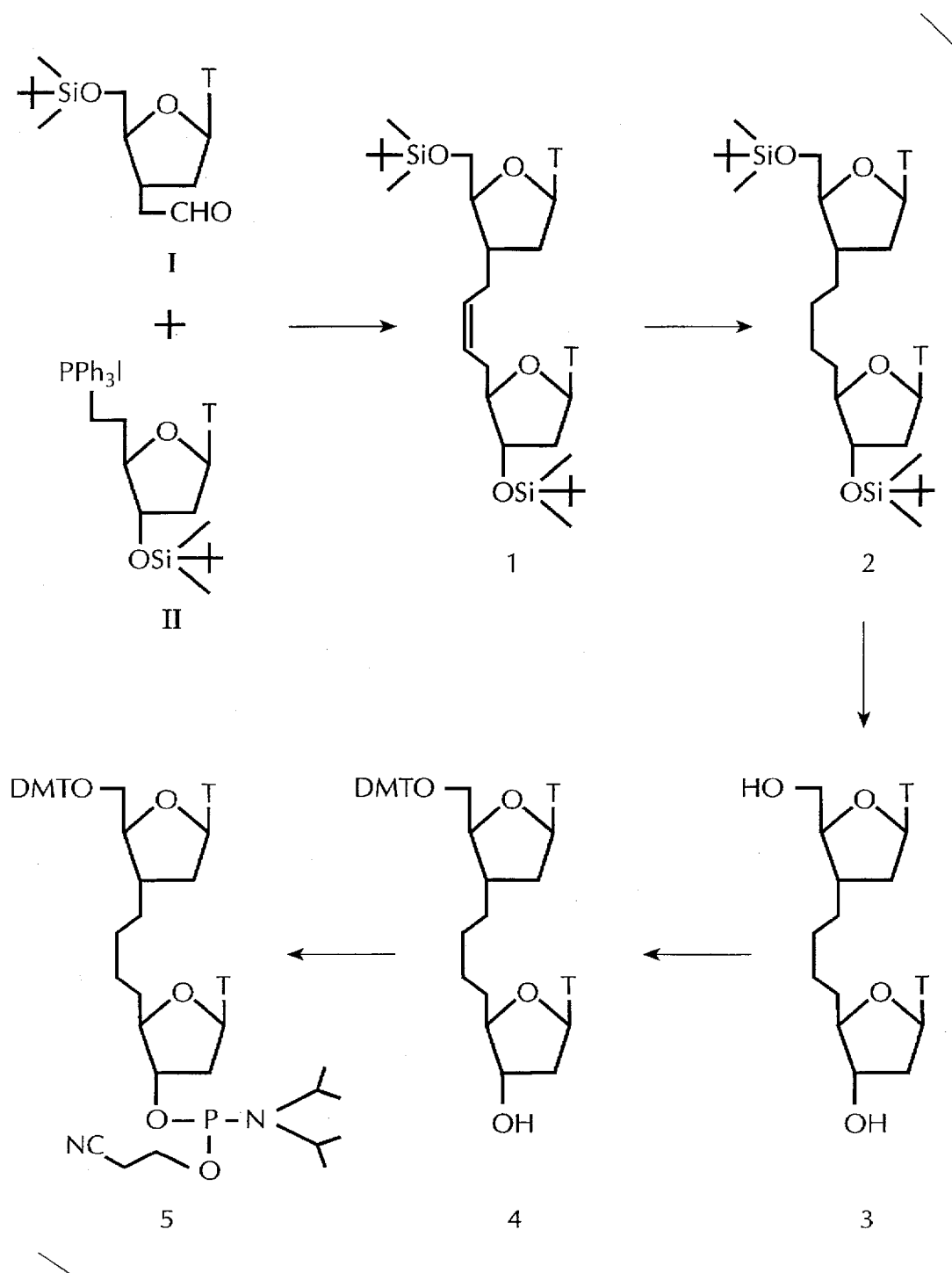
FIG. 3 depicts a synthetic pathway for preparing a thymidine dimer utilizing a thymidine aldehyde and a phosphonium iodide thymidine (Compounds I and II respectively).

The processes of example 10a–10e are illustrated in FIG. 3.

10a. To a stirred suspension of the phosphonium iodide compound prepared according to the method of Example 7 (241 mg, 0.326 mmol) in dry THF (2.0 ml) was added potassium tert-butoxide (0.62 ml, 1.0M solution in THF, 0.62 mmol) at −78° C. under nitrogen. After 20 minutes, the 3'-acetaldehyde compound prepared according to the method of Example 9 (80 mg, 0.22 mmol) was added. After 60 minutes, the reaction mixture was diluted with ethyl acetate (30 ml), washed with water (2×5 ml) and brine (5 ml) and dried (Na$_2$SO$_4$). The solvent was evaporated and the olefin product (Compound 1) was purified by flash chromatography using 70% ethyl acetate in hexane. The yield was in the range of 55–60%.

10b. 10% Pd—C (20 mg) was added to a stirred solution of Compound 1 (109 mg) in methanol (5.0 ml) at 25° C. and at 1 atmospheric pressure of hydrogen. After 4 hours, the catalyst was filtered over a pad of celite and the solvent was evaporated. Compound 2 was thus recovered and then purified by flash chromatography in 80% ethyl acetate in hexane.

10c. About 2.8 equivalents of tetrabutyl ammonium fluoride at 0° C. were added to a stirred solution of Compound 2 (350 mg) in 5.0 ml of THF. After 3 hours, the solvent was evaporated and Compound 3 was purified by flash chromatography using 10% methanol in CH$_2$Cl$_2$.

10d. About 0.05 equivalents of 4-dimethylamino pyridine, 1.4 equivalents of triethylamine and 1.2 equivalents of 4,4'-dimethoxytrityl chloride were added to a stirred solution of Compound 3 (0.6 mmol) in dry pyridine (4.0 ml). After 2 hours, the reaction mixture was quenched with 2.0 ml of water and then diluted with 2.0 ml of ethyl acetate. The organic phase was separated, washed with brine and dried. Compound 4 was purified by flash chromatography using 5% methanol in methylene chloride.

10e. About 2.0 equivalents of diisopropyl ethyl amine and 1.0 ml of dry dichloromethane (CH$_2$Cl$_2$) was added to a stirred solution of Compound 4 (0.5 mmol). After 30 minutes, 0.75 equivalents of 2-cyanoethyl-N,N-diisopropylchlorophosphoramidite was added, drop by drop over a period of 20 minutes and stirring continued for another 1 hour. The solvent was then evaporated and Compound 5 was purified by flash chromatography using ethyl acetate (containing 1% triethyl amine) under nitrogen atmosphere.

The processes of steps a–d above are used to make dimers containing three carbon internucleoside linkages in which all three carbons have the formula —CH$_2$—.

Any or all of the carbons can be optionally hydroxylated by modifying the process illustrated in FIG. 3 as follows. A drop of 2.5% (w/v) solution of osmium tetraoxide in t-butanol at 0° C. was added to a stirred solution of Compound 1 and 4-methyl morpholine N-oxide (9.1 mg) in 0.8 ml of THF. The reaction mixture was kept at 0° C. for 24 hours, quenched with an aqueous solution of sodium metabisulfite, diluted with ethyl acetate and washed with water and brine. The solvent was evaporated and the resulting hydroxylated dimer purified by thin layer chromatography using ethyl acetate as an eluent. The hydroxylated dimer is then protected and the 5' and 3' terminals modified as in steps b–d, above.

EXAMPLE 11

Preparation of hydroxylated three carbon internucleoside linkages

The thymidine-dimer phosphoramidite compounds produced by steps a–d were used in a modified solid phase phosphoramidite synthetic procedure to make the oligonucleoside sequences of Table 1.

The oligodeoxynucleotides were synthesized from the 3' to the 5' terminus.

TABLE 1

| Sequence | Ref. Code |
|---|---|
| 5' TpTpTpTpTpTp[TcT]pTpTpTpTpypypT 3' | 1 |
| 5' TpTpTpTpTpTpTp[TcT]pTpTpypypT 3' | 2 |
| 5' TpTpTpTpTpTpTpTp[TcT]pypT 3' | 3 |

T = thymidine $$p = O-\overset{\overset{O}{\|}}{\underset{\underset{O^{\ominus}}{|}}{P}}-O$$

c = —CH$_2$—CH$_2$—CH$_2$—
Y = tetraethyleneglycol

Synthesis then proceeded in accordance with a modified phosphoramidite procedure. The 5'-hydroxyl group of the attached thymidine was reacted with trichloroacetic acid to deprotect the 5'-hydroxyl group. Following this deprotection step, the attached thymidine was reacted with the activating agent, tetrazole, and a phosphoramidite reagent comprising dimethoxytrityltetraethyleneglycolcyanophosphine. The activation step was followed by the capping of unreacted 5'-hydroxyl groups with acetic anhydride and N-methylimidazole. The phosphorous linkage was then oxidized with iodine in accordance with standard procedures. In sequences 1 and 2, containing two tetraethyleneglycol (TEG) residues, the deprotecting, activating, capping and oxidizing steps were repeated as described above.

Chain elongation then proceeded via the standard sequential steps of deprotection, activation, capping and oxidation with the modification that a three-carbon linked thymidine dimer, prepared according to the methods of Examples 1–9, in the chain was added where desired during an activation step.

At the end of chain assembly, the thymidine oligomers were removed from the CPG support with concentrated ammonium hydroxide. The solution was then further treated at 55° C. for 8 to 15 hours to remove all the protecting groups on the exocyclic amines of the bases.

EXAMPLE 12

Preparation of 3'-O-acetyl-5'-carbomethoxymethyl-5'-deoxythymidine

About 0.39 g sodium borohydride was added to a cold (ice bath) stirred, mixture of 3.17 g of 3'-O-acetyl-5'-carbomethoxymethylene-5'-deoxythymidine in 95 ml isopropanol. The mixture was stirred at 0° C. under nitrogen atmosphere for half an hour, then at room temperature for an additional four and one half hours.

The chilled mixture was quenched with 20 ml methanol, followed in 30 minutes with 200 ml of distilled water, and then extracted with several portions of ethylacetate. The combined organic extracts were treated with brine and dried with anhydrous magnesium sulfate. The drying agent was filtered off and the solvent evaporated, yielding the title compound as a residual glass of 2.7 g.

EXAMPLE 13

Preparation of 5'-carbomethoxymethyl-5'-deoxythymidine

About 10 drops of a 25% (w/v) methanolic solution of sodium methoxide was added to a cold, stirred solution of 2.22 g of 3'-O-acetyl-6'-carbomethoxymethyl-5'-deoxythymidine, prepared according to the method of Example 12, in about 300 ml of dry (passed through a bed of neutral alumina) methanol. The mixture was stirred under a nitrogen atmosphere, without replenishing the ice bath, for about 20 hours.

A small amount of cation exchange resin (Bio-Rad AG 50WX8), was added and the mixture stirred for 30 minutes. The solvent was removed under reduced pressure, yielding a residual glass of 2.1 g, which was treated with warm toluene, and, after cooling, filtered and rinsed out with cyclohexane to yield a crude product as a white solid, 1.64 g.

The title compound was further purified from a trace of starting material by chromatography on silica gel, eluting with ethyl acetate, then recrystallization from ethyl acetate/hexane to yield white crystals.

EXAMPLE 14

Preparation of 3'-O-t-butyldimethylsilyl-5'-(2"-hydroxyethyl)-thymidine

About 19 ml of a 1M diisobutylaluminum hydride in tetrahydrofuran (THF) were added to a cold (−40° to −30° C.), stirred solution of 1.88 g of 3'-O-t-butyldimethylsilyl-5'-carboethoxymethyl-5'-deoxythymidine in 40 ml of anhydrous THF, under a nitrogen atmosphere. The reaction temperature was then slowly increased to −20° C.

The mixture was quenched with about 3.5 ml methanol, and the reaction temperature increased to −10° C. About 18 ml water in 36 ml THF were added to the warm mixture and the temperature further increased to 10° C. Most of the THF was removed, via reduced pressure and the residue diluted with about two volumes of water. The aqueous phase was extracted several times with ethyl acetate/chloroform. The combined extracts were washed with cold 2N hydrochloric acid, and brine, dried with anydrous magnesium sulfate and filtered. The solvent was removed from the filtrate with reduced pressure to yield the title compound (about 1.6 g).

EXAMPLE 15

Preparation of 3'-O-t-butyldimethylsilyl-5'-(2"-iodoethyl)-5'-deoxythymidine

About 1 g of p-toluenesulfonyl chloride was added to a solution of 1 g of 3'-O-t-butyldimethylsilyl-5'-(2"-hydroxyethyl)-5'-deoxythymidine, prepared according to the method of Example 14, in 25 to 30 ml of anhydrous pyridine, and the mixture maintained, stoppered, at about 5° C. for approximately 19 hours.

The mixture was added to about 200 ml of ice water and extracted several times with ether. The combined organic extracts were washed with cold 2N hydrochloric acid, water, and brine. The washed extracts were dried with anhydrous sodium sulfate and filtered. The solvent was removed from the filtrate via reduced pressure to yield a residual glass of 1.24 g of the p-toluenesulfonyl derivative.

About 0.54 g of the p-toluenesulfonyl derivative and 0.38 g sodium iodide were dissolved in 55 ml of dry (molecular sieves, 4A) acetone for three days, followed by the further addition of 0.19 g sodium iodide with stirring for a final day.

The reaction mixture was filtered and the solvent was evaporated to yield crude product.

The crude product was purified by chromatography on 85 g of silica gel eluting with 25% ethyl acetate in hexane. The solvent was evaporated to yield 0.4 g of the desired 3'-O-t-butyldimethylsilyl-5'(2"-iodoethyl)-5'-deoxythymidine.

EXAMPLE 16

Preparation of 5'-carbomethoxymethylene-5'-deoxythymidine

About 10 drops of a 25% sodium methoxide in methanol were added to a stirred solution of 1.5 g of 3'-O-acetyl-5'-carbomethoxymethylene-5'-deoxythymidine in 150 ml of dry methanol (passed through a bed of neutral alumina). The mixture was stirred at room temperature under a nitrogen atmosphere for an additional 6 hours.

A small amount of cation exchange resin (Bio-Rad AG-50W-X8) was added to the mixture with stirring for 10 minutes. The solvent was removed under reduced pressure to yield a white solid residue of 1.3 g. The residue was triturated twice with warm toluene, then taken up in hot ethanol, filtered, and chilled to yield the title compound as a white crystalline product, after drying, 0.85 g.

EXAMPLE 17

Preparation of 3'-O-t-butyldimethylsilyl-5'-(2"-hydroxyethylene)-5'-deoxythymidine A solution of 296 mg 5'-carbethoxymethylene-5'-deoxythymidine was added dropwise under a nitrogen atmosphere to a cold (ice water bath), stirred solution of 205 mg imidazole and 227 mg t-butyldimethylsilyl chloride in 1 ml of anhydrous dimethylformamide. After complete addition, the mixture was removed from the ice and stirring continued at ambient temperature for two hours, then at 35° C. for another two hours, and finally at 40° C. for half an hour.

The mixture was then quenched with 2 ml of methanol, followed by two to three volumes of water. The aqueous phase was extracted several times with ethyl acetate. The combined organic extracts were washed with water, saturated bicarbonate solution, and brine, dried with anhydrous magnesium sulfate, and filtered. The solvent was removed from the filtrate via reduced pressure to yield 0.40 g of 3'-O-t-butyldimethylsilylyl-5'-carbomethoxymethylene-5'-deoxythymidine.

About 4 ml of a 1M solution of diisobutylaluminum hydride in tetrahydrofuran was added dropwise to a −30° C. to −35° C. chilled solution of 0.37 g of the 3'-O-t-butyldimethylsilyl-5'-carbomethoxymethylene-5'-deoxythymidine dissolved in 10 ml of anhydrous tetrahydrofuran at a temperature below −30° C. After addition was complete, the reaction was stirred under a nitrogen atmosphere for an additional two hours while maintaining the internal temperature in the range of from about −30° to about −20° C.

About 0.8 ml of methanol was added to the reaction mixture followed by the addition of a solution of 4 ml water in 8 ml of tetrahydrofuran. Most of the more volatile tetrahydrofuran was removed under reduced pressure. The aqueous residue was diluted with about twice its volume of water and extracted several times with ethyl acetate. The combined organic extracts were washed with cold 1N hydrochloric acid, and brine, dried with anhydrous magnesium sulfate and filtered. The filtrate was stripped to yield the residual title compound, 0.267 g.

A portion of this material was purified to analytical purity by chromatography on silica gel, eluting with 50% ethyl acetate/hexane.

EXAMPLE 18

Preparation of thymidine dimers containing 2 two carbon-one oxygen atom (3'-O—C—C-5') internucleoside linkage 18a. To a stirred solution of 5'-O-tritylthymidine is added an equimolar amount of each of a base and 3'-O-t-butyldimethylsilyl-5'-(2"-iodoethyl)-5'-deoxythymidine at 0° C. The course of the reaction is monitored by thin layer chromatography (TLC). After the completion of the reaction, the desired dimer is isolated and purified by flash chromatography.

18b. To a stirred solution of 3'-O-t-butyldimethylsilyl-5'-(2"-hydroxyethyl)-5'-deoxythymidine maintained at a temperature of about −5° C. is added 2 equivalents of base, and the solvent is evaporated to dryness. The residue is redissolved in DMF, and an equivalent of 5'-dimethoxytrityl-2', 3'-cyclothymidine is added. The reaction mixture is heated to about 40° C., and the formation of the desired dimer is monitored by TLC. After the completion of the reaction, the desired dimer is isolated and purified by flash chromatography.

EXAMPLE 19

Deprotection of the 3' end of the dimer of Example 18

The 3'-t-butyldimethylsilyl protecting group of the protected dimers is removed by treatment of a THF solution of the dimer of Example 18 with 2.8 equivalents of tetrabutylammonium fluoride at 0° C. After the completion of the reaction (generally about 3 hours), the solvent is evaporated and the desired dimer is isolated and purified by flash chromatography.

EXAMPLE 20

Preparation of a functionalized dimer unit suitable for automated synthesis

The dimer product of Example 19 is dissolved in dichloromethane, and 2 equivalents of diisopropylethyl amine are added. The mixture is stirred for 30 minutes, followed by dropwise addition of 0.75 equivalents of 2-cyanoethyl-N,N-diisopropylchlorophosphoramidite over a period of about 20 minutes. The stirring is continued for another hour, the solvent is evaporated, and the resulting functionalized dimer is isolated and purified on a flash chromatography column using ethyl acetate under an inert atmosphere.

EXAMPLE 21

Preparation of 5'-t-butyldimethylsilyl-3'-deoxy-3'-(1",2"-dihydroxy-3"-propyl)thymidine Osmium tetraoxide ($OsO_4$) (4 drops, 2.5% w/v) in butanol was added to a stirred mixture of 3'-(2"-propenyl)-3'-deoxy-5'-O-t-butyldimethylsilyl thymidine (183 mg, 0.5 mmol), prepared according to the literature procedure, and 4-methylmorpholine-N-oxide (53 mg, 0.45 mmol) in 5.0 ml dry THF at 0° C. The reaction mixture was then quenched with 10% aqueous sodium metabisulfite (2.0 ml), stirred for 20 minutes, filtered over a pad of silica and diluted with ethyl acetate (25.0 ml). The organic phase was washed with water (5.0 ml) and brine, and then dried with $Na_2SO_4$. The solvent was evaporated and the title compound purified by flash chromatography.

EXAMPLE 22

Preparation of 3'-deoxy-thymid-3-yl-acetaldehyde-5'-O-t-butyldimethylsilylthymidine Sodium periodate (214 mg, 1 mmol) was added to a stirred solution of the thymidine diol prepared by the method of Example 21 (200 mg, 0.5 mmol) in $THF-H_2O$ (4:1 ratio, 5.0 ml). After 1 hour, the reaction mixture was diluted with ethyl acetate (25.0 ml), washed with $H_2O$ (2×5.0 ml) and brine and dried. The title compound was purified by flash chromatography with 70% ethyl acetate in hexane.

EXAMPLE 23

Preparation of 5'-o-(p-toluenesulfonyl)thymidine

To a stirred solution of thymidine (20 g, 82.6 mmol) in dry pyridine (200 ml) was added p-toluenesulfonyl chloride (47.2 g, 247.6 mmol) at 0° C. under nitrogen atmosphere. After 3 hours, the reaction mixture was poured onto ice and extracted with ethyl acetate. The solvent was evaporated and the product was crystallized from a mixture of ethyl acetate and methanol. The title compound was a white crystalline solid obtained in 70–75% yield.

EXAMPLE 24

Preparation of 5'-iodo-5'-deoxythymidine

To a stirred solution of the thymidine tosylate (10.65 g, 26.9 mmol) prepared according to the method of Example 23 in dry acetone (75 ml) was added sodium iodide (10 g, 66.7 mmol) and the mixture refluxed for 16 hours. The solvent was evaporated and diluted with ethyl acetate. The organic phase was washed with water (2×20 ml) and brine (10 ml) and dried with sodium sulfate. The title compound was crystallized from methanol as a white crystalline solid in 90–95% yield.

EXAMPLE 25

Preparation of 3'-O-t-butyldimethylsilyl-5'-iodo-5'-deoxythymidine

To a stirred solution of the thymidine iodide (8.0 g, 24.7 mmol) prepared according to the method of Example 24 in dry DMF, was added imidazole (4.2 g, 61.7 mmol). After 5 minutes tert-butyldimethyl silyl chloride (4.47 g, 29.64 mmol) was added and the mixture stirred for 4 hours. The reaction mixture was then diluted with ethyl acetate (250 ml), washed with water (2×100 ml) and brine (50 ml) and then dried with sodium sulfate. The title compound was purified by flash chromatography using 60% ethyl acetate in hexane in 92% yield.

EXAMPLE 26

Preparation of 3'-O-t-butyldimethylsilyl-5'-azido-5'-deoxythymidine

To a stirred solution of the 3'-O-t-butyldimethylsilyl-5'-iodo-5'-deoxythymidine (10.8 g, 20 mmol) prepared according to the method of Example 25 in dry DMF (50 ml) was added sodium azide (3.9 g, 60 mmol) and the mixture heated at 0° C. for 12 hours. Then the reaction mixture was diluted with ethyl acetate (200 ml) washed with water (2×50 ml) and brine (50 ml) and then dried with sodium sulfate. The title compound was purified by flash chromatography using 50% ethyl acetate in hexance in 90% yield.

EXAMPLE 27

Preparation of 3'-O-t-butyldimethylsilyl-5'-amino-5'-deoxythymidine

To a stirred solution of the thymidine azide (5.0 g, 13.1 mmol) prepared according to the method of Example 26, in MeOH was added 200 mg of 10% Pd—C under nitrogen atmosphere. The nitrogen gas was then evacuated and replaced by hydrogen. The evacuation and replacement procedure was repeated twice and stirring was continued under 1 atmospheric pressure of hydrogen for 12 hours. The hydrogen was removed and the catalyst was filtered over a pad of celite and the solvent was removed under vacuum. The crude product was purified by flash chromatography using 5–10% MeOH in $CH_2Cl_2$ to give the title compound in 85–87% yield.

EXAMPLE 28

Preparation of 3'-azido-3'-deoxy-5'-O-dimethoxyltrityl thymidine

To a stirred solution of 3'-azido-3'-deoxythymidine (2.67 g, 10 mmol) in dry pyridine (50 ml) was added 4-dimethylaminopyridine (61 mg, 0.5 mmol), triethylamine (1.9 ml, 14 mmol) and 4,4'-dimethoxytrityl chloride (4.1 g, 12 mmol) in a sequential order. After 3 hours, water (30 ml) was added and extracted with ethyl acetate (250 ml). The organic phase was separated, washed with brine (50 ml) and dried with sodium sulfate. The title compound was purified by flash chromatography using 5% methanol in methylene chloride in 80–85% yield.

EXAMPLE 29

Preparation of 3'-amino-3'-deoxy-5'-O-dimethoxytrityl thymidine

To a stirred solution of the thymidine azide (3.99 g, 40 mmol), prepared according to the method of Example 28, in MeOH was added 200 mg of 10% Pd—C under argon atmosphere. The argon gas was removed by vacuum and hydrogen was introduced. This procedure was repeated twice and stirring was continued under 1 atmosphere of hydrogen pressure for 12 hours. Then hydrogen was removed and the catalyst was filtered over a pad of celite and the solvent was removed under vacuum. The crude product was purified by flash chromatography using 5% MeOH in methylene chloride to give the title compound in 90–93% yield.

$^1$H NMR (300 MHz, $CDCl_3$) δ 7.61 (s, 1H), 7.60–7.21 (m, 1H) 6.83–6.87 (m, 3H), 6.85 (t, J=8.5 Hz, 1H), 3.80 (s, 6H), 3.81–3.73(m, 2H), 3.53–3.49(m, 1H), 3.38–3.33(m, 1H), 2.36–2.33(m, 1H), 2.25–2.20 (m, 1H), 1.51(s, 3H); IR neat vmax 3020, 2962, 1697, 1605, 1512, 1246, 1030 $cm^{-1}$.

EXAMPLE 30

Preparation of 5-O'-dimethoxytrityl-3-O'-t-butyldimethylsilyl thymidine

Dimethoxytrityl thymidine (5.0 g, 9.2 mmol) and imidazole (1.2 g, 18.4 mmol) were dissolved in 15 ml of anhydrous dimethyl formamide (DMF) and added to tert-butyldimethylsilyl chloride (1.7 g, 11.5 mmol). The reaction mixture was stirred for 4 hours at room temperature, diluted with ethyl acetate and washed with water, saturated sodium chloride and dried with sodium sulfate. A quantitative yield of the title compound was obtained.

EXAMPLE 31

Preparation of 3'-O-t-butyldimethylsilyl thymidine

5'-O-dimethoxytrityl-3'-O-t-butyldimethylsilyl thymidine prepared according to the method of Example 30 (0.7 g, 1.1 mmol) was treated for 1 hour at room temperature with 13 ml of a 3% solution of trichloracetic acid in methylene chloride. The reaction mixture was then neutralized with a 5% (w/v) sodium bicarbonate solution. The organic layer was dried with sodium sulfate. The title compound was purified by flash chromatography using a 0 to 30% gradient of ethyl acetate in methylene chloride. The yield of the reaction was 85%.

EXAMPLE 32

Preparation of 3'-O-t-butyldimethylsilyl-5'-carbethoxymethylene-5'-deoxythymidine To a well stirred solution of dry methylenechloride at −78° C. was added oxalyl chloride (33.0 mmol, 2.88 ml) followed by the dropwise addition of DMSO(3.12 ml, 44 mmol). After 10 minutes, the thymidine alcohol (5.6 g, 15.7 mmol), prepared according to the method of Example 31, in 20.0 ml of $CH_2Cl_2$ was added dropwise over a period of 2 minutes and stirring continued for 45 minutes. $Et_3N$ (8.1 ml, 58.1 mmol) was added and stirring continued for another 30 minutes. The reaction mixture was then brought to −23° C. over a period of 30 minutes. Then carbethoxy methylene triphenylphosphorane (10.94 g, 31.4 mmol) was added and the reaction mixture stirred for 12 hours at room temperature. The reaction mixture was then diluted with water (2×125 ml) and brine (50 ml) and dried ($Na_2SO_4$). The crude product was purified by flash chromatography using 20% ethyl acetate-hexane→40% ethyl acetate-hexane to give both the trans and cis isomers of the title compound in 3:1 ratio. The combined yield was about 72–76%.

Data for trans compound. IR (neat) vmax 3205, 3180, 2982, 2964, 1698, 1490, 1274 $cm^{-1}$; $^1$H NMR(300 MHz, $CDCl_3$) δ 7.04 (s, 1H), 6.87 (dd, J=15.6 and 5.4 Hz, 1H), 6.23(t, J=6.7 Hz, 1H), 6.03 (dd, J=15.6 and 1.6 Hz, 1H), 4.33–4.28 (m, 1H), 4.14(q, J=71 Hz 2H) 4.16–4.12 (m, 1H) 2.28–2.19 (m, 1H), 2.09–1.98 (m, 1H) 1.87 (s, 3H), 1.23 (t, J=7.1 Hz, 3H), 0.81 (s, 9H) 0.01 (s, 6H); Calcd for $C_{20}H_{32}O_6N_2Si$; C, 56.58; H, 7.60; N, 6.60; Found: C, 56.36; H, 7.30; N, 6.60.

EXAMPLE 33

Preparation of 3'-O-t-butyldimethylsilyl-5'-carbethoxymethyl-5'-deoxythymidine

To a stirred solution of the unsaturated thymidine ester (4.24 g, 10 mmol), prepared according to the method of Example 32, in EtOAc was added 200 mg of 10% Pd—C under nitrogen atmosphere. The nitrogen gas was removed by vacuum and hydrogen was introduced. This procedure was repeated twice and stirring was continued under 1 atmospheric pressure of hydrogen for 16 hours. Then the catalyst was filtered over a pad of celite and the solvent was removed under vacuum. The product was crystallized from a mixture of hexane and ethyl acetate. The title compound was obtained in 95% yield.

IR(neat) vmax 3180, 2925, 2950, 1696, 1486, 1260, 1240 cm$^{-1}$; $^1$H NMR (300 MHz, CDCl$_3$) δ 7.20 (s, 1H), 6.11 (t, 6.6=Hz, 1H) 4.07 (q, J=7.1 Hz, 2H), 4.03–3.98 (m, 1H), 3.73–7.69 (m, 1H), 2.51–2.32 (m, 2H), 2.24–2.15 (m, 1H), 1.18 (t, J=7.1 Hz, 3H), 0.81 (s, 9H), 0.01 (s, 6H), Anal. Calcd for C$_{20}$H$_{34}$O$_6$N$_2$Si: C, 56.31; H, 8.03; N, 6.57 Found: C, 55.91; H, 7.74; N, 6.50.

EXAMPLE 34

Preparation of 3'-O-t-butyldimethylsilyl-5'-deoxy-thymid-5-yl-acetaldehyde

To a stirred solution of the thymidine ester (3.41 g, 8 mmol), prepared according to the method of Example 33, in 60 ml of dry CH$_2$Cl$_2$ at –78° C. was added DiBAL-H (16.4 ml, 1.0M solution in hexane, 16.4 mmol) dropwise over a period of 3 min. After 20 minutes, the reaction mixture was diluted with 300 ml of EtOAc and washed with 50 ml of saturated sodium potassium tartrate solution twice. The organic phase was washed with brine (25 ml) and dried (Na$_2$SO$_4$). The title compound was purified by flash chromatography using 50%–70% ethyl acetate-hexane in 85–87% yield.

EXAMPLE 35

Preparation of a deoxythymidine dimer having a 3'-C—C—N-5' internucleoside linkage (FIG. 3)

Figure 6:
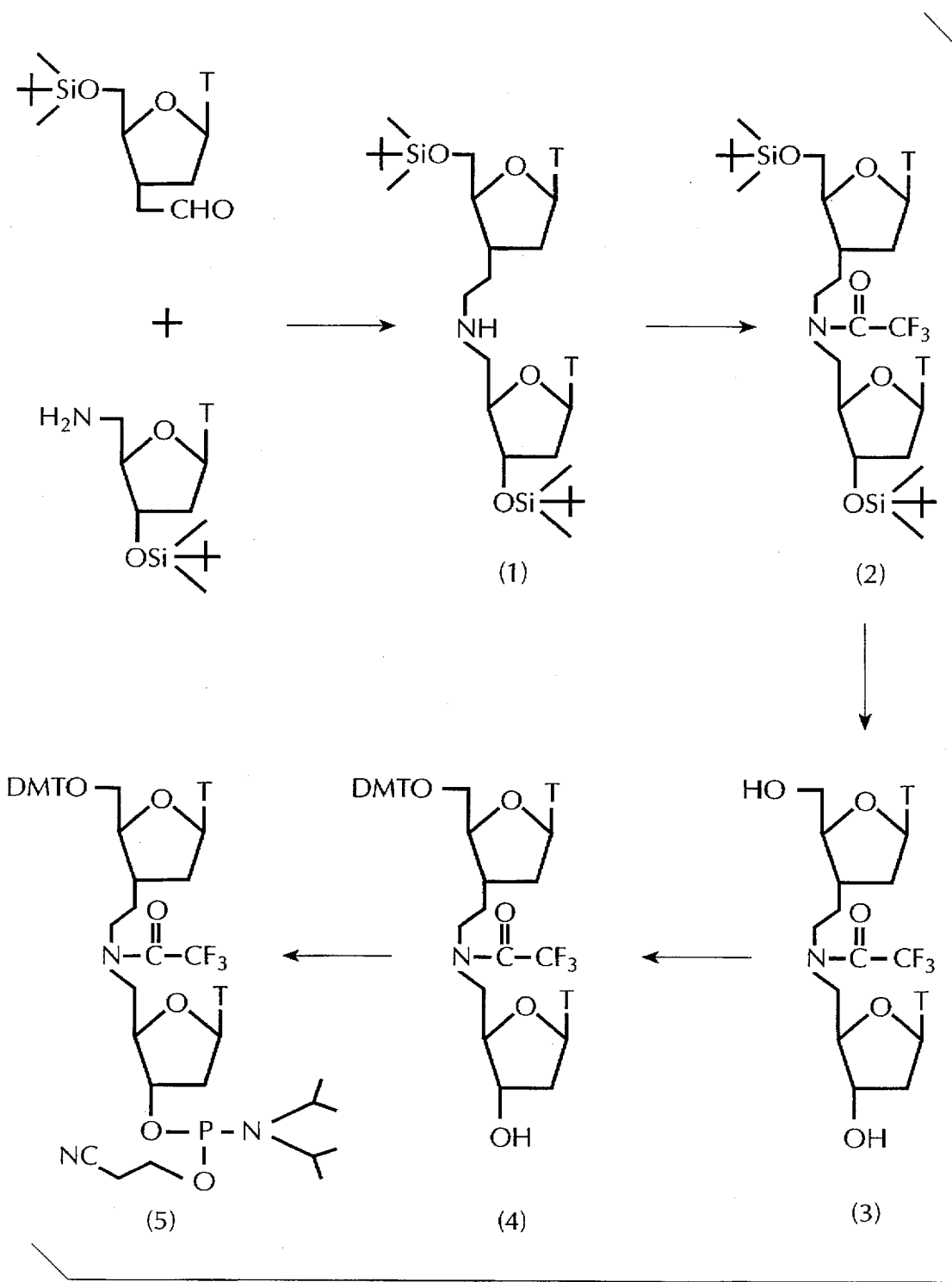
FIG. 6 depicts a synthetic pathway for preparing a thymidine dimer connected by a two carbon-one nitrogen atom internucleoside linkage of the form 3'-C—C—N-5'. Dimers are synthesized by reacting thymidines that contain aldehydes (CHO) with thymidines that contain amine functionalities ($NH_2$) under reductive conditions.

35a. To a stirred solution of the thymidine amine from Example 27 (1.07 g, 3 mmol) and the thymidine aldehyde of Example 22 (1.38 g, 3.6 mmol) in 50 ml of ethanol and 10 ml of aqueous buffer solution (pH=5.5, NaH$_2$PO$_4$—NaOH) was added a solution of NaCNBH$_3$ in THF (12 mL, 1.0M solution in THF, 12 mmol) dropwise at 5° C. over a period of 1 hour. The reaction mixture was stirred for another 4 hours and diluted with 2.50 ml of ethyl acetate. The reaction mixture was washed with water (2×40 ml) and brine (25 ml) and dried (Na$_2$SO$_4$). Compound 1 (FIG. 6) was purified by flash chromatography by first eluting with ethyl acetate followed by 5→8% MeOH—CH$_2$Cl$_2$ in 62–64% yield.

$^1$H NMR (300 MHz, CDCl$_3$) δ 7.60 (s, 1H), 7.19 (s, 1H), 6.18 (t, J=6.6 Hz, 1H), 6.08 (t, J=3.9 Hz, 1H), 4.29–4.23 (m, 1H), 4.15–3.98 (m, 1H), 3.91–1.85 (m, 1H), 3.70–3.78 (m, 2H), 2.95–2.87 (m, 1H), 2.84–2.66 (m, 3H), 2.35–2.05 (m, 5H), 1.94 (s, 3H), 1.93 (s, 3H), 1.80–1.63 (m, 1H ), 1.55–1.45 (m, 1H), 0.93 (s, 9H), 0.69 (s, 9H), 0.11 (s, 6H), 0.07 (s, 6H).

35b. Compound 1 (FIG. 6) (166 mg, 0.23 mmol) was added to a stirred solution of trifluoroacetic anhydride (0.32 ml, 2.3 mmol) and triethylamine (0.64 ml, 4.6 mmol) in CH$_2$Cl$_2$ (5.0 ml). After 2 hours, the reaction mixture was quenched with aqueous NaHCO$_3$ (5.0 ml) and diluted with EtOAc (25 ml). The organic phase was washed with water (2×10 ml), brine (5 ml) and dried (Na$_2$SO$_4$). Compound 2 (FIG. 6) was purified by flash chromatography using 7% MeOH in CH$_2$Cl$_2$ in 91–93% yield.

35c. To a stirred solution of Compound 2 (164 mg, 0.2 mmol) in THF (4.0 ml) was added tetrabutyl-ammonium fluoride (0.8 mmol) at 0° C. After 2 hours, the solvent was evaporated and Compound 3 (FIG. 6) was purified by flash chromatography using 5%–8% MeOH in CH$_2$Cl$_2$ in 90% yield.

35d. To a stirred solution of Compound 3 (151 mg, 0.26 mmol) in dry pyridine ( 3.0 ml) was added 4,4-dimethylaminopyridine (1.6 mg, 0.0128 mmol) and triethylamine (0.057 ml, 0.42 mmol). After 5 minutes, dimethoxytritylchloride (121 mg, 0.358 mmol) was added and stirring continued. After 2 hours, the reaction mixture was diluted with ethyl acetate (25 ml) and washed with water (2×10 ml), brine (5 ml) and dried (Na$_2$SO$_4$). The crude product was purified by flash chromatography using 7% MeOM in CH$_2$Cl$_2$ to give Compound 4 (FIG. 3) in 85–87% yield.

35e. Dry diisopropyl ethylamine (0.15 ml, 0.67 mmol) was added to Compound 4 (150 mg, 0.168 mmol) followed by dry CH$_2$Cl$_2$ (0.5 ml). Then the flask was shaken to dissolve the alcohol and 2-cyanoethyl-N,N-diisopropylchlorophosphoramidite (0.056 mL, 0.25 mmol) was added over a period of 20 seconds. After 45 minutes, the reaction mixture was quenched with CH$_3$OH (1.0 ml), diluted with EtOAc (50 ml) and Et$_3$N (1.0 ml), washed with 10% aqueous K$_2$CO$_3$ (2×5.0 ml), followed by brine (5.0 ml) and dried (Na$_2$SO$_4$). The crude product was purified by flash chromatography using EtOAc to give Compound 5 (FIG. 6) in 70–75% yield.

EXAMPLE 36

Preparation of a deoxythymidine dimer having a 3'-N—C—C-5'-internucleoside linkage (FIG. 4)

Figure 7:
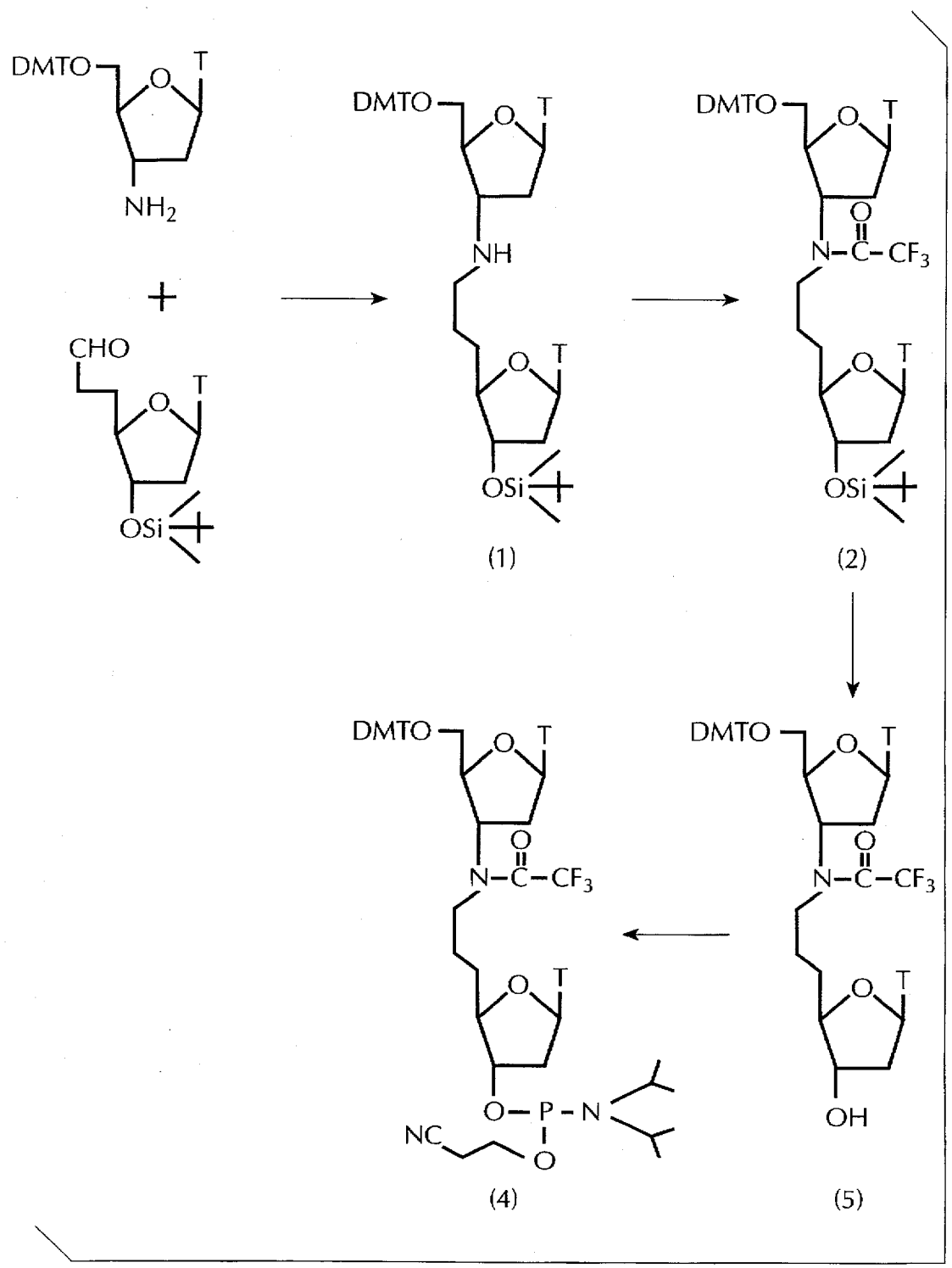
FIG. 7 depicts a synthetic pathway for preparing a thymidine dimer connected by a two carbon-one nitrogen atom internucleoside linkage of the form 3'-N—C—C-5'. Dimers are synthesized by reacting thymidines having aldehyde and amine functionalities under reductive conditions.

36a. To a stirred solution of the amine of Example 29 (2.72 g, 5 mmol) and the aldehyde of Example 34 (2.29 g, 6 mmol) in 50 ml of ethanol and 10 ml of aqueous buffer solution (pH=5.5, NaH$_2$PO$_4$—NaOH) was added a solution of NaCNBH$_3$ in THF (12 ml, 1.0M solution in THF, 12 mmol) dropwise at 5° C. over a period of 1 hour. The reaction mixture was stirred for another 4 hours and then diluted with 250 ml of ethyl acetate. The reaction mixture was washed with water (2×60 ml) and brine and dried (Na$_2$SO$_4$). Compound 1 (FIG. 7) was purified by flash chromatography by first eluting with ethyl acetate followed by 5% MeOH—CH$_2$Cl$_2$. Compound 1 (FIG. 7) was obtained in 72–74% yield.

$^1$H NMR (300 MHz, CDCl$_3$) δ 7.56 (m, 1H), 7.36–7.34 (m, 2H), 7.29–7.15 (m, 8H), 7.03 (s, 1H), 6.77 (m, 3H), 6.20 (t, J=6.0 Hz, 1H), 6.08 (t, J=6.7 Hz, 1H) 4.01–3.97 (m, 2H), 3.84–3.72 (m, 1H), 3.72 (s, 6H), 3.71–3.63 (m, 1H), 3.48–3.32 (m, 2H), 3.30–3.22 (m, 1H), 3.48–3.32 (m, 2H), 3.30–3.22 (m, 1H), 7.52 (m, 2H), 2.27–2.14 (m, 3H), 2.08–1.97 (m, 1H), 1.83 (s, 3H), 1.67–1.48 (m, 3H), 1.43 (s, 3H), 1.22–1.15 (m, 1H), 0.82 (s, 9H), 0.01 (s, 6H).

36b. To a stirred solution of trifluoroacetic anhydride (0.32 ml, 2.3 mmol) and triethylamine (0.64 ml, 4.6 mmol) in CH$_2$Cl$_2$ (5.0 ml) was added Compound 1 (FIG. 7) (210 mg, 0.23 mmol). After 2 hours, the reaction was quenched with aqueous NaHCO$_3$ (5.0 ml) and diluted with EtOAc (25 ml). The organic phase was washed with water (2×10 ml), brine (5 ml) and dried (Na$_2$SO$_4$). Compound 2 (FIG. 7) was purified by flash chromatography using 7% MeOH in CH$_2$Cl$_2$. Compound 2 was obtained in 89–91% yield.

36c. To a stirred solution of Compound 2 (180 mg, 0.2 mmol) in THF (4.0 ml) was added tetrabutylammonium fluoride (0.4 ml, 1.0M solution in the THF, 0.4 mmol) at 0° C. After 2 hours, the solvent was evaporated and the product was purified by flash chromatography using increasing polarity, 5–8% MeOH, in CH$_2$Cl$_2$ to give Compound 3 (FIG. 7) in 89% yield.

36d. Dry diisopropyl ethyl amine (0.15 ml, 0.67 mmol) was added to Compound 3 (150 mg, 0.168 mmol) followed by the addition of dry CH$_2$Cl$_2$ (0.5 ml). Then the flask was shaken to dissolve the alcohol and 2-cyanoethyl-N, N-diisopropylchlorophosphoramidite (0.056 ml, 0.25 mmol) was added over a period of 20 seconds. After 45 minutes the reaction mixture was quenched with CH$_3$OH (0.1 ml) and diluted with EtOAc (50 ml) and Et$_3$N (1.0 ml) and washed with 10% aqueous K$_2$CO$_3$ (2×5.0 ml), and brine (5.0 ml) and dried (Na$_2$SO$_4$). The product was purified by flash chromatography using EtOAc to give Compound 4 in 70–75% yield.

EXAMPLE 37

Synthesis of deoxythymidine oligomers containing a 3'-N—C—C-5' internucleoside linkage The thymidine-dimer phosphoramidite compounds produced by steps a–d above were used in a modified solid phase phosphoramidite synthetic procedure to make the oligonucleoside sequences of Table 2.

TABLE 2

| Sequence | Ref. Code |
| --- | --- |
| 5' TpTpTpTpTpTpTpTp[TnT]pT 3' | 4 |
| 5' TpTpTpTpTp[TnT]pTpTpTpT 3' | 5 |
| 5' [TnT]pTpTpTpTpTpTpTpT 3' | 6 |
| T = thymidine | |

$$p = -O-\overset{\overset{\displaystyle O}{\|}}{\underset{\underset{\displaystyle O^{\ominus}}{|}}{P}}-O-$$

n = 3'-N—C—C-5'

The oligodeoxynucleoside sequences were synthesized from the 3' to the 5' terminus.

The initial step was the attachment, via a 3'-succinate linkage, of a 5'-dimethoxytrityl deoxythymidine to a CPG support. The 5'-O-dimethoxytrityl group of the attached thymidine was reacted with trichloroacetic acid to deprotect the 5'-hydroxyl group.

Chain elongation then proceeded via the standard sequential steps of deprotection, activation, capping and oxidation with the modification that an —N—C—C— linked thymidine dimer, prepared according to the methods of Examples 30–37, was added in the chain where desired during an activation step.

At the end of chain assembly, the thymidine oligomers were removed from the CPG support with concentrated ammonium hydroxide. The solution was then further treated at 55° C. for 8 to 15 hours to remove all the protecting groups on the exocyclic amines of the bases.

EXAMPLE 38

Preparation of Tetraethyleneglycol-terminated Anti-RAS oncogene DNA

38a. Preparation of dimethoxytrityltetraethyleneglycol (DMTTEG)

An excess of tetraethyleneglycol TEG (about 100 ml) was admixed with about 7 ml (5.1 g; 40 mmols) of Hunig's base in a round bottom flask. About 3.08 g (10 mmols) of dimethoxytrityl chloride (DMTCl) was added to the TEG admixture and the DMTCl-TEG mixture maintained with constant stirring at room temperature (about 25° C.) for about 8 to 12 hours to form DMTTEG.

38b. Preparation of dimethoxytrityltetraethyleneglycolcyanophosphine (DMTTEGCP).

Six grams of the DMTTEG from step (a) was admixed with 20 ml of dry dichloromethane. About 6.2 ml of Hunig's base was added to the admixture, followed by the dropwise addition of a chlorophosphine mixture to form DMTTEGCP. The chlorophosphine mixture was prepared by dissolving 1.67 g of 2-cyanoethyl N,N-diisopropylchlorophosphoramidite in 5 ml of dry dichloromethane.

38c. Preparation of TEG-terminated Anti-BAS oncogene DNA.

The oligodeoxynucleotides of Table 3 were prepared according to a modified solid phase phosphoramidite method. GAIT, supra. The oligodeoxynucleotides were synthesized from the 3' to the 5' terminus.

TABLE 3

| Sequence | Ref. Code |
| --- | --- |
| 5' X GGA GCT GGT GGC GTA X (A) 3' | 7 |
| 5' XX GGA GCT GGT GGC GTA XX (A) 3' | 8 |
| 5' X CCT CGA CCA CCG CAT X (A) 3' | 9 |
| 5' XX CCT CGA CCA CCG CAT XX (A) 3' | 10 |
| 5' CCT CGA CCA CCG CAT 3' | 11 |

X is TEG

A, C, G & T represent the deoxynucleotides adenylic, cytidylic, guanidylic and thymidylic acids, respectively.

Either the nucleoside adenosine (7, 8, 9, 10) or thymidine (11) was attached to a CPG solid support using a succinate linkage. GAIT, supra. The synthesis of 11 proceeded in accordance with standard solid phase phosphoramidite procedures. In sequences 7, 8, 9 and 10, synthesis proceeded in accordance with a modified phosphoramidite procedure. The 5' hydroxyl group of the attached adenosine nucleoside was reacted with trichloroacetic acid to deprotect the 5' hydroxyl group. Following this deprotection step, the attached adenosine nucleoside was reacted with the activating agent, tetrazole, and a phosphoramidite reagent comprising DMTTEGCP, prepared by the processes of steps a and b above. The activation step was followed by the capping of unreacted 5' hydroxyl groups with acetic anhydride and N-methylimidazole. The phosphorous linkage was then oxidized with iodine in accordance with standard procedures.

In sequences 8 and 10, containing two TEG residues, the deprotecting, activating, capping and oxidizing steps were repeated as described above. Chain elongation proceeded via the sequential steps of deprotection, activation, capping and oxidation as described above with the modification that the desired nucleoside phosphoramidite reagent was substituted for the DMTTEGCP during the activation step. Following attachment of the last desired nucleoside, either one or two TEG residues were attached at the 5' terminal in a manner analogous to the attachment of TEG at the 3' terminus.

At the end of chain assembly, the DNA strand was removed from the CPG support with concentrated ammonium hydroxide. The solution was then further treated at 55° C. for 8 to 15 hours to remove all the protecting groups on the exocyclic amines of the bases.

EXAMPLE 39

Preparation of hexaethyleneglycol (HEG)-terminated Anti-RAS oncogene DNA

Hexaethyleneglycol (HEG) terminated anti-RAS oncogene DNA was prepared according to the methods of Example 38. HEG was reacted with DMTCl to form DMTHEG. The DMTHEG was then reacted with a cyanophosphine compound to form DMTHEGCP, which was used in the modified solid phase phosphoramidate synthesis method of Example 38(c) to form HEG-terminated anti-RAS oncogene DNA. The sequences of these oligonucleotides are set forth in the following Table 4.

TABLE 4

| Sequence |
| --- |
| 5' X GGA GCT GGT GGC GTA X (A) 3' |
| 5' XX GGA GCT GGT GGC GTA XX (A) 3' |
| 5' X CCT CGA CCA CCG CAT X (A) 3' |
| 5' XX CCT CGA CCA CCG CAT XX (A) 3' |
| 5' CCT CGA CCA CCG CAT 3' |

X is HEG

A, C, G & T represent the deoxynucleotides adenylic, cytidylic, guanidylic and thymidylic acids, respectively.

EXAMPLE 40

Nuclease Resistance of TEG-terminated Anti-RAS oncogene DNA

The oligonucleotides of Table 4 were dissolved in water. DNA concentrations were then determined by measuring the absorbance of samples at 260 nm (on a Perkin Elmer Lambda 4C Spectrophotometer at ambient room temperature) and using calculated extinction coefficients [method of Cantor and Warsaw, *CRC Handbook of Biochemistry and Molecular Biology*, 3rd. ed. Vol. 1, CRC Press, page 589 (1975)].

The oligonucleotides were incubated for 2 hours at 37° C. at a total strand concentration of 6 or 7 µM in cell culture medium containing RPMI 1640; 20 mM N-(2-hydroxyethyl) piperazine-N'-(2-ethanesulfonic acid), pH 7.4; and 10% fetal calf serum (FCS) (GIBCO Laboratories, Grand Island, N.Y.). The FCS was heat inactivated at 56° C. for 0.5 hour prior to use. Samples were then placed on ice and deproteinized using five extractions with 24:1 chloroform:isoamyl alcohol. Samples were either stored frozen at −20° C. or immediately loaded onto a refrigerated (4° C.) WISP (Waters) HPLC autoinjector.

Oligonucleotide hydrolysis was guantitated by determining the amount of disappearance of the parent compound. Oligonucleotides (from the reaction mixture) were separated on an LKB Ultrachrome GTi dual pump chromatography system equipped with a fixed wavelength detector (260 nm), and recording integrator, using a GenPak FAX (Waters) anion exchange column eguilibrated in Buffer A (1 mM EDTA; 15 mM sodium phosphate, pH 8.5). Column temperature was maintained at 60° C. using a Waters column oven. Fifty microliter sample injection volumes were used. The oligonucleotides were eluted using a linear gradient of 0% to 100% Buffer B (Buffer A containing 0.5M NaCl) over 60 minutes. Buffer flow rate was 1 mL/min.

Following incubation (2 hrs) in the presence of fetal calf serum-associated exonuclease, no degradation of compounds 7 or 10 was observed (Table 5, see % degradation of major peak). During a similar incubation period, 87.0% and 82.1% of 9 and 8, respectively, remained. In comparison, only 24.7% of oligomer 11 remained after the same incubation period.

TABLE 5

| SAMPLE ID | AREA-MAJOR PEAK/0.0 MIN | AREA-MAJOR PEAK/2.0 HR | % DEGRADATION MAJOR PEAK |
| --- | --- | --- | --- |
| 7 | 0.2325 | 0.3663 | 0.0 |
| 9 | 0.3744 | 0.3258 | 13.0 |
| 8 | 0.2164 | 0.1777 | 17.9 |
| 10 | 0.3642 | 0.3697 | 0.0 |
| 11 | 1.2861 | 0.3177 | 75.3 |

All four TEG-oligomers were resistant to hydrolysis by the FCS-associated exonucleases. The bis-diTEG-oligomers (7 and 10) appeared to be completely resistant to hydrolysis. TEG-derivatized oligodeoxynucleotides represent significant improvements over unmodified compounds in terms of resistance to exonuclease hydrolysis.

EXAMPLE 41

Ability of TEG-Antisense Oligomers to Inhibit Protein Expression and Growth in Human Tumor Cell Lines and PHA Stimulation of Peripheral Blood Lymphocytes It has been demonstrated by others (Heikkila, R. et al., *Nature*, 328:445–449, 1987) that unmodified antisense oligonucleotides directed towards the initiation codon region of the c-myc oncogene could inhibit the expression of c-myc protein in PHA stimulated peripheral blood lymphocytes (PBL) resulting in a block in the progression of cells into the S-phase of the cell cycle. C-myc directed antisense DNA was also shown to inhibit the growth of HL-60 human erytholeukemia cells in vitro (Wickstrom, E. L., et al., *Proc. Natl. Acad. Sci. USA*, 85:1028–1032, 1988). The sequentes shown in Table 6 were prepared and evaluated by the procedures of Example 41a and 41b.

TABLE 6

| 5' AAC GTT GAG GGG CAT 3' |
| --- |
| 5' XX AAC GTT GAG GGG CAT XX A 3' |

(X = TEG)

41a. Comparison of the Effect of Modified (with TEG) and Non-Modified C-MYC Antisense DNA on the Progression of PHA Stimulated PBL Into the S-Phase of the Cell Cycle.

Human PBL's were stimulated with PHA for 48 hours in the presence or absence of the antisense oligonucleotide sequences of Table 6. The percent of the population of cells in each treatment group in the S-phase of the cell cycle as compared to the nontreated control was determined using standard flow cytometric techniques. The results are shown in Table 7.

TABLE 7

| OLIGONUCLEOTIDE | CONCENTRATION (μM) | % CONTROL S-PHASE |
|---|---|---|
| NONE | | 100 |
| 5' AAC GTT GAG GGG CAT 3' | 30 | 75 ± 6 |
| | 60 | 9 ± 10 |
| 5' XX AAC GTT GAG GGG CAT XX A 3' | 30 | 80 ± 4 |
| | 60 | <6 |

The data show that the presence of TEG at both the 3' and 5' termini does not alter the inhibitory effect of the antisense DNA.

41b. comparison of the Effect of Modified (with TEG) and Non-Modified C-MYC Antisense DNA on C-MYC Protein Expression in MOLT-4 Human T-Cell Leukemia Cells.

Asynchronous exponentially growing Molt-4 cells were incubated for 8 hours in the presence or absence of 60 μM c-myc directed antisense DNA. The cells were then incubated for 45 minutes in the presence of $^{35}$S-methionine and the content of c-myc protein guantitated using radioimmunoprecipitation with a c-myc antibody. The results are displayed in Table 8.

required to inhibit cell growth by 50% was then determined ($IC_{50}$), Both of the modified and non-modified antisense DNAs of Table 5 displayed approximately equivalent ($IC_{50}$) concentrations of 40 μM.

These data demonstrate that the presence of TEG at the 3' and 5' termini of antisense DNA does not affect the ability of such antisense DNA to hybridize with and inhibit the function of target nucleic acids.

EXAMPLE 42

Additional Exonuclease Stable Oligonucleotides

The exonuclease stable digonucleotides set forth in Table 9 were prepared according to the methods of Example 38.

TABLE 8

| OLIGO-NUCLEOTIDE | CONCENTRATION (μM) | % REDUCTION C-MYC PROTEIN |
|---|---|---|
| NONE | | 0 |
| 5' AAC GTT GAG GGG CAT 3' | 60 | 61.0 ± 2.6 |
| 5' XX AAC GTT GAG GGG CAT XX A 3' | 60 | 67.9 ± 0.7 |

The TEG containing antisense DNA was slightly more potent than the unmodified antisense DNA.

41c. Comparison of the Effect of Modified (with TEG) and Unmodified C-MYC Antisense DNA to Inhibit the Growth of Human CCRF-CEM T-Cell Leukemia Cell Growth in Vitro.

Asynchronous exponentially growing CCRF-CEM cells were incubated for 48 hours in the presence or absence of antisense DNA and then cell numbers determined in each treatment group. The concentration of antisense DNA

TABLE 9

```
5' XX  A—ACG—TTG—AGG—GGC—ATX—XA        3'
   XX  GCC—CGC—CTC—GGT—CCC—CGC—CCX—XA
   XX  GGG GCG GAG TTA GGG GCG GCG GGX XA
   XX  GGG—GAG—GAG—GGA—GGG—GAG—GGA—XXA
   XX  GGG—GAG—GTG—GGT—GGG—GAG—GGT—XXA
       AAG GTT GAG GGG CAT XXA
   X   AA—CGT—TGA—GGG—GCA—TTX—A
   XX  TTC—GCT—TAC—CAG—AGT=XXA
   XX  GCG—GGA—GGC—TGC—TGG—XXA
   XX  GGA—GGC—TGC—TGG—AGC—XXA
   XX  CAA—GTT—CAT—AGG—TGA—TTG—CTC—XXA
   AL—CAC—TCC—TTT—AGC—AAG—XXA
   AL—GAA—CGA—TTT—CCT—CAC—XXA
   XX  CTC—ACT—GCC—GCG—CAT—XXA
   XX  GGG—TCT—TCG—GGC—CAT—XXA
   XX  GTC—GAC—CGG—TTC—CAT—XXA
   XX  TGT—AAC—TGC—TAT—AAA—XXA
   XX  GTT—CCT—CCT—CTT—TAA—XXA
   XX  TAC—TGC—CTT—ATA—TTC—XXA
   XX  TAC—TGA—CTT—ATA—TTT—XXA
   XX  TTT—ATA—TTC—AGT—CAT—XXA
```

TABLE 9-continued

```
XX  TGG—GGA—GGG—TGG—GGA—GGG—TGG—GGA—AGG—XXA
XX  CTT—ATA—TTC—CGT—CAT—XXA
XX  TAA—CGC—CTA—TTC—TGC—XXA
XX  CGT—CTT—ATC—CGC—AAT—XXA
XX  TTG—CTC—TCC—TCT—GTC—XXA
XX  CTG—TCT—CCT—CTC—GTT—XXA
XX  ATC—TAC—TGG—CTC—CAT—XXA
XX  TAC—CTC—GGT—CAT—CTA—XXA
XX  ACA—CCC—AAT—TCT—GAA—ATG—GXX—A
XX  GGT—AAA—GTC—TTA—ACC—CAC—AXX—A
XX  TAC—GGG—GAG—TTG—CAA—XXA
```

X is TEG

As will be apparent to those skilled in the art, many variations and modifications may be made without departing from the spirit and scope of the present invention.

We claim:

1. A compound consisting essentially of an oligonucleoside sequence of from about 6 to about 200 bases having a three atom internucleoside linkage of the formula:

—D—D—D—;

having hexaethyleneglycol or tetraethyleneglycol at either or both termini where each D is independently CHR, oxygen or $NR^6$, wherein R is independently hydrogen, OH, SH or $NH_2$, wherein $R^6$ is hydrogen or $C_1$–$C_2$-alkyl, with the proviso that only one D is oxygen or $NR^6$.

2. The compound according to claim 1 consisting essentially of bases selected from the group consisting of adenine, cytosine, guanine, uracil and thymine.

3. The compound according to claim 1 which has from about 9 to about 50 bases.

4. The compound according to claim 1 which has from about 12 to about 25 bases.

5. A pharmaceutical composition comprising a physiologically acceptable carrier and a compound comprising oligonucleoside sequences of from about 6 to about 200 bases having a non-phosphate containing three atom internucleoside linkage of the formula:

—D—D—D—;

having hexaethyleneglycol or tetraethyleneglycol at either or both termini where each D independently CHR, oxygen or $NR^6$ wherein R is independently hydrogen, OH, SH or $NH_2$, $R^6$ is hydrogen or $C_1$–$C_2$-alkyl, with the proviso that only one D is $NR^6$.

6. The pharmaceutical composition according to claim 5 wherein the oligonucleoside sequence has the formula:

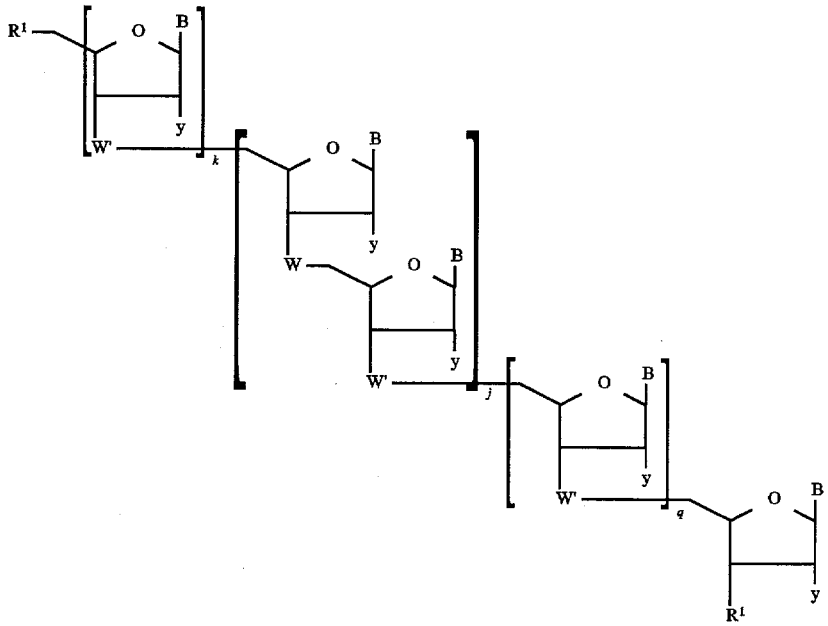

where W is —D—D—D— wherein each D is independently CHR, oxygen or $NR^6$, wherein R is independently hydrogen, OH, SH, or $NH_2$, $R^6$ is hydrogen or $C_1$–$C_2$ alkyl, with the proviso that only one D is oxygen or $NR^6$;

each W' is independently W or

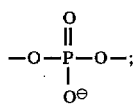

each $R^1$ is independently OH, SH, $NR^2R^3$ wherein $R^2$ and $R^3$ are independently hydrogen or $C_1$–$C_6$ alkyl or $NHR^4$ wherein $R^4$ is $C_1$–$C_{12}$ acyl;

each y is independently H or OH;

each B is independently adenine, cytosine, guanine, thymine or uracil;

j is an integer from 1 to 200;

k is 0 or an integer from 1 to 197; and q is 0 or an integer from 1 to 197, with the proviso that the sum of j+k+q is from 4 to 200.

7. The pharmaceutical composition according to claim 6 wherein the compound comprises bases selected from the group consisting of adenine, cytosine, guanine, uracil and thymine.

8. The pharmaceutical composition according to claim 6 wherein the compound has from about 6 to about 50 bases.

9. The pharmaceutical composition according to claim 6 wherein the compound has from about 12 to about 25 bases.

10. The pharmaceutical composition according to claim 5 wherein the compound has hexaethyleneglycol or tetraethyleneglycol at either or both termini.

11. A compound consisting essentially of an oligonucleoside sequence of the formula:

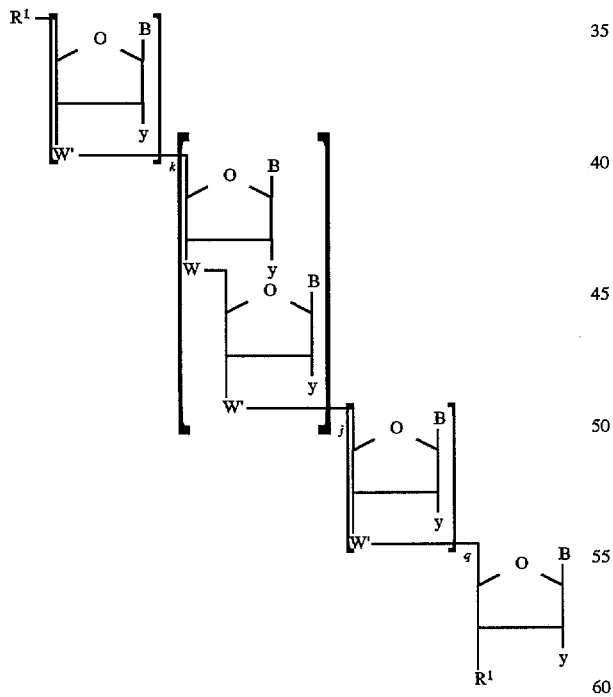

where W is —D—D—D— wherein each D is independently CHR, oxygen or $NR^6$, wherein R is independently hydrogen, OH, SH, or $NH_2$, $R^6$ is hydrogen or $C_1$–$C_2$ alkyl, with the proviso that only one D is oxygen or $NR^6$, each W' is independently W or

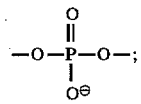

each $R^1$ is independently OH, SH, $NR^2R^3$ wherein $R^2$ and $R^3$ are independently hydrogen or $C_1$–$C_6$ alkyl or $NHR^4$ wherein $R^4$ is $C_1$–$C_{12}$ acyl;

each y is independently H or OH;

each B is independently adenine, cytosine, guanine, thymine and uracil;

j is an integer from 1 to 200;

k is 0 or an integer from 1 to 197; and q is 0 or an integer from 1 to 197, with the proviso that the sum of j+k+q is from 4 to 200.

12. The compound according to claim 11 consisting essentially of bases selected from the group consisting of adenine, cytosine, guanine, uracil and thymine.

13. The compound according to claim 11 which has from about 9 to about 50 bases.

14. The compound according to claim 11 which has from about 12 to about 25 bases.

15. A compound consisting essentially of an oligonucleoside sequence of from about 6 to about 200 bases having the formula:

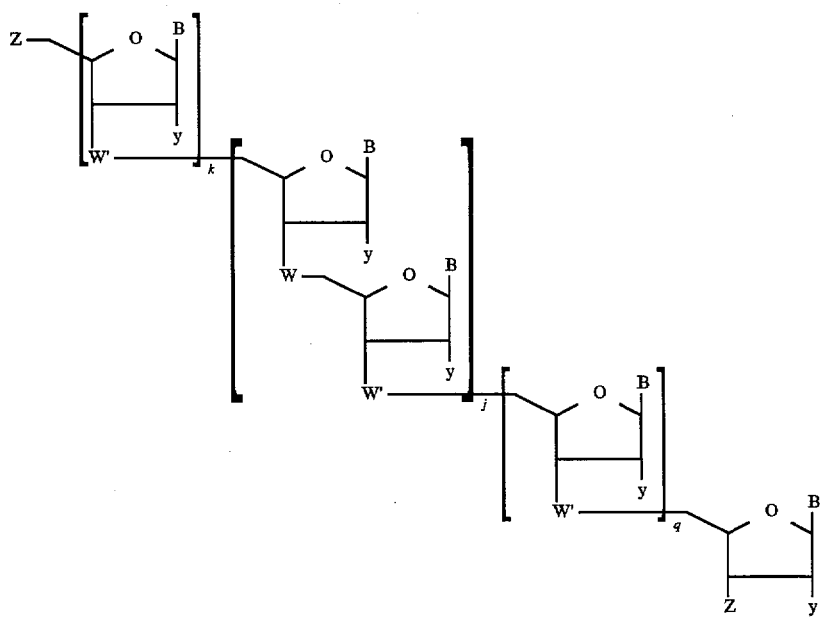

where each Z is independently R' or

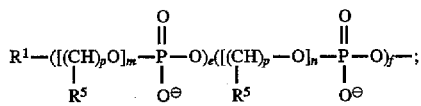

where W is —D—D—D— wherein each D is independently CHR, oxygen or $NR^6$, wherein R is independently hydrogen, OH, SH or $NH_2$, $R^6$ is hydrogen or $C_1$–$C_2$ alkyl, with the proviso that only one D is oxygen or $NR^6$;

each W' is independently W or

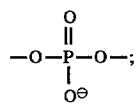

each $R^1$ is independently OH, SH, $NR^2R^3$ wherein $R^2$ and $R^3$ are independently hydrogen or $C_1$–$C_6$ alkyl or $NHR^4$ wherein $R^4$ is $C_1$–$C_{12}$ acyl;

each $R^5$ is independently hydrogen or $C_1$–$C_{12}$ alkyl;

each y is independently H or OH;

each B is independently adenine, cytosine, guanine, thymine or uracil;

each e and f is independently an integer from 0 to 50, with the proviso that at least one of e and f be at least 1;

j is an integer from 1 to 200;

k is 0 or an integer from 1 to 197; and each m and n is independently an integer from 1 to 200;

each p is independently 2 to 4; and q is 0 or an integer from 1 to 197, with the proviso that the sum of j+k+q is from 4 to 200.

16. The compound according to claim 15 consisting essentially of bases selected from the group consisting of adenine, cytosine, guanine, uracil and thymine.

17. The compound according to claim 15 which has from about 9 to about 50 bases.

18. The compound according to claim 15 which has from about 12 to about 25 bases.

19. A nuclease resistant compound consisting essentially of an oligonucleotide sequence of from about 9 to about 200 bases having hexaethyleneglycol or tetraethyleneglycol at either or both termini.

20. A compound according to claim 19 wherein the ethyleneglycol is hexaethyleneglycol.

21. A compound according to claim 19 wherein the ethyleneglycol is tetraethyleneglycol.

22. A compound according to claim 19 wherein the oligonucleotide sequence has from about 9 to about 50 bases.

23. A compound according to claim 19 wherein the oligonucleotide sequence has from about 12 to about 25 bases.

24. A compound consisting essentially of an oligonucleotide of the formula:

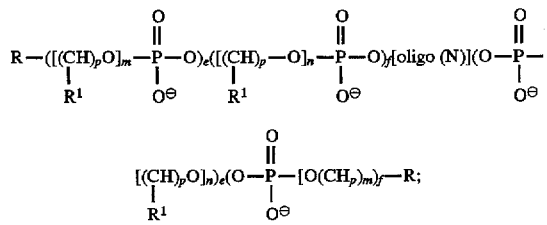

where R is OH, SH, $NR^2R^3$ wherein $R^2$ and $R^3$ are independently hydrogen or $_1$-$C_6$ alkyl, or $NHR^4$ wherein $R^4$ is $C_1$–$C_{12}$ acyl;

$R^1$ is hydrogen or $C_1$–$C_{12}$ alkyl;

oligo (N) is a native or modified oligonucleotide sequence of from 9 to 200 bases;

each e and f is independently 0 to 50, with the proviso that at least one of e and f be at least 1;

each m and n is independently 1 to 200; and each p is independently 2 to 4.

25. A compound according to claim 24, wherein oligo (N) is a homopolymer or heteropolymer sequence containing any combination of deoxyadenylic acid, deoxycytidylic acid, deoxyguanidylic acid and thymidylic acid.

26. A compound according to claim 24 wherein oligo (N) is a homopolymer or heteropolymer sequence containing any combination of adenylic acid, cytidylic acid, guanidylic acid and uridylic acid.

27. A compound according to claim 24 wherein m and n are independently 1 to 8.

28. A compound according to claim 24 wherein both m and n are 4.

29. A compound according to claim 24 wherein both m and n are 6.

30. A compound according to claim 24 wherein the oligonucleotide sequence is from about 9 to about 50 bases.

31. A compound according to claim 24 wherein the oligonucleotide sequence is from about 12 to about 25 bases.

32. A compound consisting essentially of an oligonucleotide of the formula:

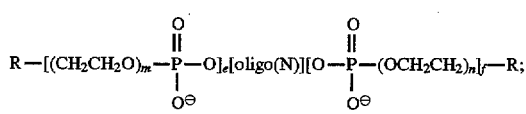

where R is OH, SH, $NR^2R^3$ wherein $R^2$ and $R^3$ are independently hydrogen or $C_1$–$C_6$ alkyl, or $NHR^4$ wherein $R^4$ is $C_1$–$C_{12}$ acyl;

oligo N is an oligonucleotide sequence of from 9 to 50 bases;

and e and f are independently 0 to 50, with the proviso that at least one of e and f be at least one; and m and n are independently 0 to 200 with the proviso that at least one of m and n be 1 to 200.

33. A compound according to claim 32, wherein oligo (N) is a homopolymer or heteropolymer sequence containing any combination of deoxyadenylic acid, deoxycytidylic acid, deoxyguanidylic acid and thymidylic acid.

34. A compound according to claim 32 wherein oligo (N) is a homopolymer or heteropolymer sequence containing any combination of adenylic acid, cytidylic acid, guanidylic acid and uridylic acid.

35. A compound according to claim 32 wherein m and n are independently 1 to 8.

36. a compound according to claim 32 wherein both m and n are 4.

37. A compound according to claim 32 wherein both m and n are 6.

38. A compound according to claim 32 wherein the oligonucleotide sequence is from about 9 to about 50 bases.

39. A compound according to claim 32 wherein the oligonucleotide sequence is from about 12 to about 25 bases.

40. A method of inhibiting nuclease degradation of a compound consisting of oligonucleoside sequences of from about 6 to about 200 bases having a three atom internucleoside linkage of the formula:

—D—D—D—;

where each D is independently CHR, oxygen or $NR^6$, wherein R is independently hydrogen, OH, SH or $NH_2$, $R^6$ is hydrogen, or $C_1$–$C_2$-alkyl, with the proviso that only one D is oxygen or $NR^6$, comprising attaching hexaethyleneglycol or tetraethyleneglycol to said compound at either or both termini.

41. The method according to claim 40 wherein the oligonucleoside sequences have the formula:

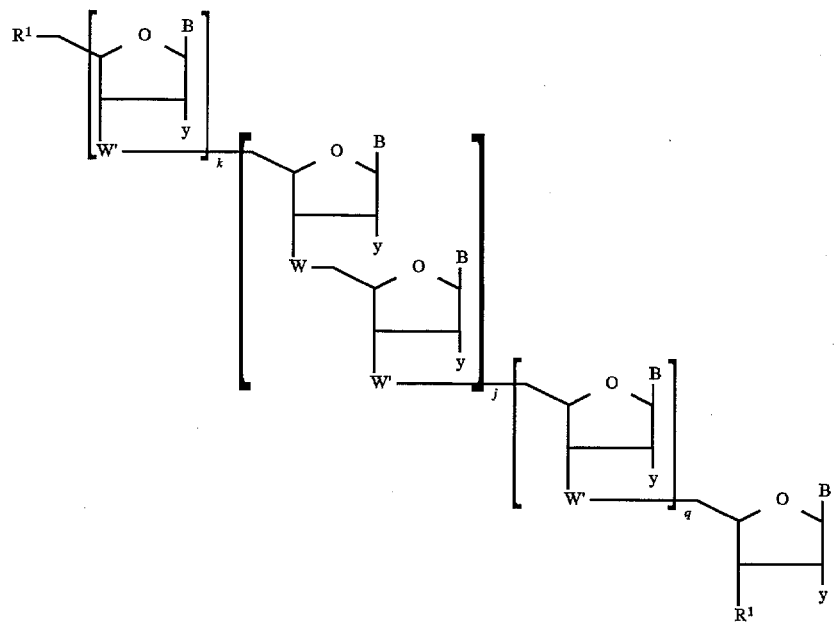

where W is —D—D—D— wherein each D is independently CHR, oxygen or $NR^6$, wherein R is independently hydrogen, OH, SH, or NH$_2$, R$^6$ is hydrogen or C$_1$–C$_2$ alkyl, with the proviso that only one D is oxygen or NR$^6$;

each W' is independently W or

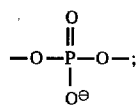

each R$^1$ is independently OH, SH, NR$^2$R$^3$ wherein R$^2$ and R$^3$ are independently hydrogen or C$_1$–C$_6$ alkyl or NHR$^4$ wherein R$^4$ is C$_1$–C$_{12}$ acyl;

each y is independently H or OH;

each B is independently adenine, cytosine, guanine, thymine or uracil;

j is an integer from 1 to 200;

k is 0 or an integer from 1 to 197; and q is 0 or an integer from 1 to 197, with the proviso that the sum of j+k+q is from 4 to 200.

42. The method according to claim 41 wherein the oligonucleoside sequences comprise bases selected from the group consisting of adenine, cytosine, guanine, uracil and thymine.

43. The method according to claim 41 wherein the compound has from about 6 to about 50 bases.

44. The method according to claim 41 wherein the compound has from about 12 to about 25 bases.

45. The method according to claim 41 wherein the compound has hexaethyleneglycol or tetraethyleneglycol at either or both termini.

46. A compound consisting essentially of a nucleoside dimer of the formula:

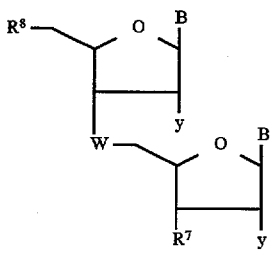

where W is —D—D—D— wherein each D is independently CHR, oxygen or NR$^6$, wherein R is independently hydrogen, OH, SH or NH$_2$, R$^6$ is hydrogen or C$_1$–C$_2$ alkyl, with the proviso that only one D is oxygen or NR$^6$;

each B is independently adenine, cytosine, guanine, thymine or uracil;

R$^7$ is OH, t-butyldimethylsilyloxy or a phosphoramidite; and

R$^8$ is OH, a protecting group or t-butyldimethylsilyloxy.

47. The compound according to claim 46 wherein R$^8$ is dimethoxytrityl.

48. The compound according to claim 46 wherein R$^7$ is cyanoethyl-N,N-diisopropyl-phosphoramidite.

49. A method of stabilizing nucleotide or oligonucleotide sequences comprising attaching an alkylene glycol residue to either or both termini of said nucleotide or oligonucleotide by contacting with a dimethoxytritylglycolcyanophosphine.

50. A method according to claim 49 wherein the dimethoxytritylglycolcyanophosphine is dimethoxytrityltetraethyleneglycolcyanophosphine or dimethoxytritylhexaethyleneglycolcyanophosphine.

51. The method according to claim 50 wherein said dimethoxytritylglycolcyanophosphine is used to protect the 5'-terminus of said compound.

52. A pharmaceutical composition comprising a nuclease resistant compound comprising an oligonucleotide sequence of from about 9 to about 200 bases having hexaethyleneglycol or tetraethylenglycol at either or both termini and a physiologically acceptable carrier.

53. A composition according to claim 52 wherein the diol is a polyalkyleneglycol.

54. A composition according to claim 52 wherein the diol is polyethyleneglycol.

55. A composition according to claim 52 wherein the diol is hexaethyleneglycol or tetraethyleneglycol.

56. A composition according to claim 52 wherein the compound comprises an oligonucleotide of the formula:

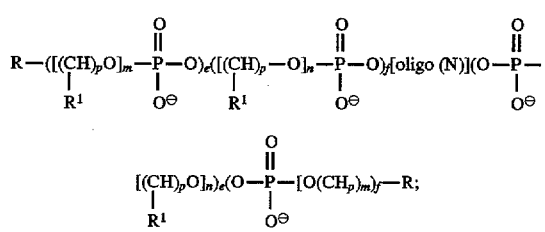

here R is OH, SH, NR$^2$R$^3$ wherein R$^2$ and R$^3$ are independently hydrogen or $_1$-C$_6$ alkyl, or NHR$^4$ wherein R$^4$ is C$_1$–C$_{12}$ acyl;

R$^1$ is hydrogen or C$_1$–C$_{12}$ alkyl;

oligo (N) is a native or modified oligonucleotide sequence of from 9 to 200 bases;

each e and f is independently 0 to 50, with the proviso that at least one of e and f be at least 1;

each m and n is independently 1 to 200; and each p is independently 2 to 4.

57. A composition according to claim 56 wherein oligo (N) is a homopolymer or heteropolymer sequence containing any combination of deoxyadenylic acid, deoxycytidylic acid, deoxyguanidylic acid and thymidylic acid.

58. A composition according to claim 56 wherein oligo (N) is a homopolymer or heteropolymer sequence containing any combination of adenylic acid, cytidylic acid, guanidylic acid and uridylic acid.

* * * * *